US006943171B2

(12) United States Patent
Asberom et al.

(10) Patent No.: US 6,943,171 B2
(45) Date of Patent: Sep. 13, 2005

(54) POLYCYCLIC GUANINE DERIVATIVE PHOSPHODIESTERASE V INHIBITORS

(75) Inventors: Theodros Asberom, West Orange, NJ (US); John W. Clader, Cranford, NJ (US); Yueqing Hu, Kowloon (HK); Dmitri A. Pissarnitski, Scotch Plains, NJ (US); Andrew W. Stamford, Chatham Township, NJ (US); Ruo Xu, Watchung, NJ (US)

(73) Assignee: Schering Corporation, Kenilworth, NJ (US)

( * ) Notice: Subject to any disclaimer, the term of this patent is extended or adjusted under 35 U.S.C. 154(b) by 186 days.

(21) Appl. No.: 10/290,011

(22) Filed: Nov. 7, 2002

(65) Prior Publication Data

US 2003/0176413 A1 Sep. 18, 2003

Related U.S. Application Data

(60) Provisional application No. 60/344,498, filed on Nov. 9, 2001.

(51) Int. Cl.[7] .................... C07D 487/14; A61K 31/519; A61P 15/10; A61P 9/12; A61P 9/04
(52) U.S. Cl. ..................... 514/257; 544/251; 544/231; 540/559; 540/555; 514/267
(58) Field of Search ............................... 544/251, 231; 540/559, 555

(56) References Cited

U.S. PATENT DOCUMENTS

| | | | |
|---|---|---|---|
| 5,250,534 A | 10/1993 | Bell et al. .................... 514/258 |
| 5,256,766 A | 10/1993 | Coughlin .................... 530/327 |
| 5,346,901 A | 9/1994 | Bell et al. .................... 514/258 |
| 5,393,755 A | 2/1995 | Neustadt et al. .......... 514/233.2 |
| 5,409,934 A | 4/1995 | Smith et al. ................. 514/263 |
| 5,470,579 A | 11/1995 | Bonte et al. ................. 424/450 |
| 5,688,768 A | 11/1997 | Coughlin et al. ............. 514/15 |
| 5,719,283 A | 2/1998 | Bell et al. .................... 544/262 |
| 5,759,994 A | 6/1998 | Coughlin et al. .............. 514/9 |
| 5,798,248 A | 8/1998 | Coughlin et al. ........... 435/214 |
| 5,824,683 A | 10/1998 | McKittrick et al. ......... 514/257 |
| 5,856,448 A | 1/1999 | Coughlin ............... 530/388.22 |

(Continued)

FOREIGN PATENT DOCUMENTS

| | | |
|---|---|---|
| EP | 0 389 282 A2 | 9/1990 |
| EP | 0 526 004 A1 | 7/1992 |
| EP | 0 463 756 B1 | 4/1995 |
| EP | 0 702 555 B1 | 3/1996 |
| FR | 2 116 302 A | 7/1972 |
| WO | 89/10123 | 11/1989 |
| WO | 91/19717 | 12/1991 |
| WO | WO 91/19717 | 12/1991 |
| WO | 92/05175 | 4/1992 |
| WO | 92/05176 | 4/1992 |
| WO | 93/23401 | 11/1993 |
| WO | 94/19351 | 9/1994 |
| WO | WO 94/19351 | 9/1994 |
| WO | 94/28902 | 12/1994 |

(Continued)

OTHER PUBLICATIONS

Suzuki, Chem Pharm Bull 50(9) 1163 (2002).*
U.S. Appl. No. 60/383,478, filed May 31, 2002, Dahanukar.
U.S. Appl. No. 60/384,484, filed May 31, 2002, Dahanukar.
U.S. Appl. No. 09/940,760, filed Aug. 28, 2001, Chackalamannil.
U.S. Appl. No. 10/227,778, filed Aug. 26, 2002, Asberom.
Ho–Sam Ahn et al, "Potent Tetracyclic Guanine Inhibitors of PDE1 and PDE5 Cyclic Guanosine Monophosphate Phosphodiesterases with Oral Antihypertensive Activity", *J. Med. Chem.*, vol. 40, No. 14, pp. 2196–2210 (1997).
Kent S. Allenby et al, "Pentoxifylline in the Treatment of Vascular Impotence—Case Reports", pp. 418–420 (1991).
J.L. Ambrus et al, "Studies on Vasoocclusive Crisis of Sickle Cell Disease. I. Effect of Pentoxifylline", *Journal of Medicine*, vol. 10, No. 6, pp. 445–456 (1979).
Bradley D. Anderson et al, "Preparation of Water–Soluble Compounds Through Salt Formation", The Practice of Medicinal Chemistry, C. G. Wermuth, Ed., *Academic Press*, New York, pp. 739–754 (1996).

(Continued)

Primary Examiner—Mark L. Berch
(74) Attorney, Agent, or Firm—Gerard E. Reinhardt

(57) ABSTRACT

A compound having the formula (Ia) or (b), salt or solvate thereof, with the variables as defined herein, which can inhibit selectively phosphodiesterase V and can be useful for treating sexual dysfunction and other physiological disorders, symptoms and diseases:

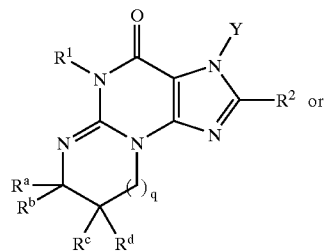

(Ia)

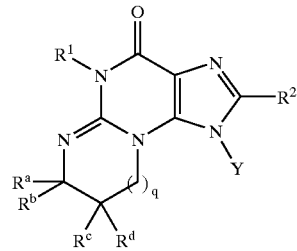

(Ib)

14 Claims, No Drawings

U.S. PATENT DOCUMENTS

| | | | |
|---|---|---|---|
| 5,859,006 A | 1/1999 | Daugan | 514/249 |
| 5,874,437 A | 2/1999 | Garvey et al. | 514/258 |
| 5,877,216 A | 3/1999 | Place et al. | 514/573 |
| 5,939,419 A | 8/1999 | Tulshian et al. | 514/257 |
| 5,958,926 A | 9/1999 | Garvey et al. | 514/253 |
| 5,981,527 A | 11/1999 | Daugan et al. | 514/250 |
| 6,024,936 A | 2/2000 | Coughlin et al. | 424/1.49 |
| 6,025,494 A | 2/2000 | Daugan | 546/64 |
| 6,037,346 A | 3/2000 | Doherty, Jr. et al. | 514/258 |
| 6,100,270 A | 8/2000 | Campbell | 514/258 |
| 6,124,101 A | 9/2000 | Coughlin | 435/7.1 |
| 6,140,329 A | 10/2000 | Daugan | 514/250 |
| 6,143,746 A | 11/2000 | Daugan et al. | 514/249 |
| 6,197,541 B1 | 3/2001 | Coughlin | 435/69.1 |
| 6,362,178 B1 | 3/2002 | Niewöhner et al. | 514/218 |
| 6,403,597 B1 | 6/2002 | Wilson et al. | 514/256 |
| 6,469,012 B1 | 10/2002 | Ellis et al. | 514/258 |
| 6,469,016 B1 | 10/2002 | Place et al. | 514/262 |
| 6,472,434 B1 | 10/2002 | Place et al. | 514/573 |
| 6,512,002 B2 | 1/2003 | Lee et al. | 514/427 |
| 2003/0153587 A1 * | 8/2003 | Asberom et al. | 544/251 |

FOREIGN PATENT DOCUMENTS

| | | |
|---|---|---|
| WO | 96/16644 | 6/1996 |
| WO | 96/16657 | 6/1996 |
| WO | 96/32379 | 10/1996 |
| WO | 97/03985 | 2/1997 |
| WO | 97/24334 | 7/1997 |
| WO | 97/43287 | 11/1997 |
| WO | 98/08848 | 3/1998 |
| WO | 98/15530 | 4/1998 |
| WO | 98/38168 | 9/1998 |
| WO | 98/49166 | 11/1998 |
| WO | 99/00359 | 1/1999 |
| WO | 99/00373 | 1/1999 |
| WO | 99/21558 | 5/1999 |
| WO | 99/21831 | 5/1999 |
| WO | 99/24433 | 5/1999 |
| WO | 99/42452 | 8/1999 |
| WO | 99/43674 | 9/1999 |
| WO | 99/43679 | 9/1999 |
| WO | 99/54333 | 10/1999 |
| WO | 99/62905 A | 12/1999 |

OTHER PUBLICATIONS

M.I. Argel et al, "Effect of Phosphodiesterase Inhibitors on Heart Contractile Behavior, Protein Kinase Activity and Cyclic Nucleotide Levels", *J. Mol. Cell Cardiol,* vol. 12, No. 10, pp. 939–954, Abstract (1980).

Hans–Joachim Arnold et al, "Pharmacopoeia of Traditional Medicine in Venda", *Journal of Ethnopharmacology,* vol. 12, pp. 35–74 (1984).

William J. Aronson et al,"The Mediator of Human Corpus Cavernosum Relaxation is Nitric Oxide", *The Journal of Urology,* vol. 145, No. 4, p. 341A, Abstract No. 516 (1991).

Joseph A. Beavo, "Cyclic Nucleotide Phosphodiesterases: Functional Implications of Multiple Isoforms", *Physiological Reviews,* vol. 75, No. 5, pp. 725–748 (Oct. 1995).

Joseph A. Beavo & David H. Reifsnyder, "Primary sequence of cyclic nucleotide phosphodiesterase isozymes and the design of selective inhibitors", *Trends in Pharmacological Sciences,* vol. 11, No. 4, pp. 150–155 (Apr. 1990).

Stephen M. Berge et al, "Pharmaceutical Salts", J. of *Pharmaceutical Sciences,* Am. Pharm Assoc. and Pergamon Press, vol. 66, No. 1, pp. 1–19 (Jan. 1977).

Anne Bowman et al, "Cyclic GMP mediates neurogenic relaxation in the bovine retractor penis muscle", *Br. J. Pharmac.,* vol. 81, pp. 665–674 (1984).

V. Mirone et al, letter to ed. re. "Intracavernous Cyclic GMP Products Produces Penile Erection in Patients with Erectile Dysfunction", *British Journal of Urology,* vol. 71, No. 3, p. 365 (Mar. 1993).

Gary Brooker et al, "Radioimmunoassay of Cyclic AMP and Cyclic GMP", *Advances in Cyclic Nucleotide Research,* Paul Greengard et al, Eds., vol. 10, pp. 1–33 (1979).

Margaret Ann Bush, "The role of the L–arginine–nitric oxide–cyclic GMP pathway in relaxation of corpus cavernosum smooth muscle", Ph.D. dissertation U.C.L.A. (UMI Dissertation Services Order No. 9319914) (179 pgs) (1993).

Peggy Bush et al, "Nitric Oxide is a Potent Relaxant of Human and Rabbit Corpus Cavernosum", *Journal of Urology,* vol. 147, pp. 1650–1655 (Jun. 1992).

S. Carrier et al, "Erectile Dysfunction," *Endocrinology and Metabolism Clinics of North America: Clinical Andrology,* vol. 23, No. 4, pp. 773–782 (Dec. 1994).

P. Cazzulani et al, "Pharmacological Activities of the Main Metabolite of Flavoxate 3–Methylflavone–8–carboxylic Acid", *Drug Res.,* vol. 38 (I), No. 3, pp. 379–382 (1988).

J. Cortijo et al, "Investigation into the role of Phosphodiesterase IV in Bronchorelaxation, including Studies with Human Bronchus", *Br. J. Pharmacol.,* vol. 108, pp. 562–568 (1993).

Jacob de Boer et al, "Human bronchial cyclic nucleotide phosphodiesterase isoenzymes: biochemical and pharmacological analysis using selective inhibitors", *Br. J. Pharmacol.,* vol. 106, pp. 1028–1034 (1992).

Dario Doller et al, "The GIF System as a Tool in Medicinal Chemistry: The Oxidation of SCH57726 under GOAGG III Conditions", *Bioorganic and Medicinal Chemistry Letters,* vol. 7, No. 11, pp. 1381–1386 (1997).

I.J. Fishman, "Treating Erectile Dysfunction: New Approaches", *Drug Therapy,* vol. 8, pp. 102–110 (Aug. 1989).

P.G. Gillespie & J.A. Beavo, "Inhibition and Stimulation of Photoreceptor Phosphodiesterases by Dipyridamole and M & B 22,948", *Molecular Pharmacology,* vol. 36, pp. 773–781 (Nov. 1988).

J.C. Gingell, et al, "Emerging pharmacological therapies for erectile dysfunction", *Exp. Opin. Ther. Patents,* vol. 9, No. 12, pp. 1689–1696 (1999).

Philip L. Gould, "Salt Selection for Basic Drugs", *Int'l J. of Pharmaceutics,* Elsevier, vol. 33, pp. 201–217 (1986).

Theodora W. Greene, "Protective Groups in Organic Synthesis", John Wiley & Sons, Inc., New York, pp. 1–9 (1981).

Alain Gregoire, "Viagra: on release", *BMJ,* vol. 317, p. 759–760 (Sep. 19, 1998).

"Pharmaceutical Coloring Agents", Handbook of Pharmaceutical Excipients, American Pharmaceutical Association & the Pharmaceutical Society of Great Britain, pp. 81–90 (1986).

Takeru Higuchi, "Prodrug & Drug Delivery—An Overview", Bioreversible Carriers in Drug Design: Theory and Application, Edward B. Roche, Ed., Pergamon Press, New York, pp. 1–12 (1987).

T. Higuchi et al, Eds., "Pro–drugs as Novel Drug Delivery Systems", ACS Symposium Series 14, American Chemical Society, Wash., D.C., pp. 1–115 (1975).

F. Holmquist et al, "Actions of 3–Morpholinosydnonimin (SIN–1) on Rabbit Isolated Penile Erectile Tissue", *Journal of Urology,* vol. 150, No. 4, pp. 1310–1315 (Oct. 1993).

F. Holmquist et al, "Effects of the nitric oxide synthase inhibitor $N^G$–nitro–L–arginine on the erectile response to cavernous nerve stimulation in the rabbit", *Acta Physiol Scand,* vol. 143, pp. 299–304 (1991).

Sue Ellen Jackson et al, "Erectile Dysfunction: Therapy Health Outcomes", *Outcomes Research, Pfizer, Inc.,* Elsevier (Dec. 16, 1997).

T. Katsushima et al, "Structure–Activity Relationships of 8–Cycloalkyl–1,3–dipropylxanthines as Antagonists of Adenosine Receptors", *J. Med. Chem,* vol. 33, pp. 1906–1910 (1990).

Yasuo Kawanishi et al, "Double–Blind Trial of Oral Prostaglandin $E_1$ on Impotence", *The Japanese Urological Association,* vol. 83, No. 1, Abstract, pp. 1655–1661 (Oct. 1992).

Stanley G. Korenman et al, "Treatment of Vasculogenic Sexual Dysfunction with Pentoxifylline," *J. Am. Geriatrics Soc.,* vol. 41, No. 4, pp. 363–366 (Apr., 1993).

Robert J. Krane et al, "Impotence", *New England Journal of Medicine,* vol. 321, No. 24, pp. 1648–1658 (Dec. 14, 1989).

W.R. Kukovetz et al, "Evidence for Cyclic GMP–Mediated Relaxant Effects of Nitro–Compounds in Coronary Smooth Muscle", *Naunyn–Schmiedeberg's Archives of Pharmacology,* vol. 310, pp. 129–138 (1979).

Y.–M. Lin et al, "The rabbit as an intracavernous injection study model", *Urol. Res,* vol. 24, pp. 27–32 (1996).

Tom F. Lue, "Topical and Oral Agents for Erectile Dysfunction", *J. Formos Med. Assoc,* vol. 98, No. 4, pp. 233–242(Mar. 9, 1999).

James A. Lugg et al, "The Role of Nitric Oxide in Erectile Function," *J. of Andrology,* vol. 16, No. 1, pp. 2–4 (Jan./Feb. 1995).

E.G. McMahon et al, "Depressor and Natriuretic Effects of M & B 22,948, a Guanosine Cyclic 3',5'–Monophosphate–Selective Phosphodiesterase Inhibitor", *Journal of Pharmacology and Experimental Therapeutics,* vol. 2513, pp. 1000–1005 (1989).

W. Meinhardt et al, "The influence of medication on erectile function", *International Journal of Impotence Research,* vol. 9, pp. 17–26 (1997).

M.F. Meyer et al, "Intracavernous Application of SIN–I in Rabbit and Man: Functional and Toxicological Results", *Ann. Urol.,* vol. 27, No. 3, pp. 179–182 (1993).

Alvaro Morales et al, "Oral and Topical Treatment of Erectile Dysfunction", *Urologic Clinics of North America,* vol. 22, No. 4, pp 879–886 (Nov. 1995).

John E. Morley, "Management of Impotence, Diagnostic considerations and therapeutic options", *Impotence,* vol. 93, No. 3, pp. 65–67, 71–72 (Feb. 15, 1993).

Kenneth J. Murray, "Phosphodiesterase $V_A$ Inhibitors," *Drug News and Perspectives,* vol. 6, No. 3, pp. 150–156 (Apr. 1993).

C. David Nicholson et al, "Differential modulation of tissue function and therapeutic potential of selective inhibitors of cyclic nucleotide phosphodiesterase isoenzymes", *Trends in Pharmacological Sciences,* vol. 12, pp. 19–27 (Jan. 1991).

Elizabeth Palmer, "Making the love drug", *Chemistry in Britain,* vol. 35, No. 1, pp. 24–26 (Jan. 1999).

Pfizer, "Erectile Dysfunction", 1998 Annual Report, p. 21.

Physicians' Desk Reference, Medical Economics Company, 55th Ed., pp. 2534–2537 (2001).

Physician's Desk Reference, Medical Economics Company, 46th Ed., pp. 1099–1100 (1992).

Physician's Desk Reference, Medical Economics Company, 46th Ed., Product Identification Dayton Himbin Tablets and Yohimex Tablets, pp. 409, 905 & 1190 (1992).

Jacob Rajfer et al, "Nitric Oxide as a Mediator of Relaxation of the Corpus Cavernosum in Response to Nonadrenergic, Noncholinergic Neurotransmission", *New England Journal of Medicine,* vol. 326, No. 2, pp. 90–94 (Jan. 9, 1992).

J. Reiser et al, "The Effect of Zaprinast (M&B 22, 948, on Orally Absorbed Mast Cell Stabilizer) on Exercise–Induced Asthma in Children", *Br. J. Dis. Chest.,* vol. 80, pp. 157–163 (1986).

Remington's Pharmaceutical Sciences, "Coloring, Flavoring and Diluting Agents", 18th Ed., A.R. Gennaro, Ed., Mack Publishing Co., pp. 1288–1300 (1990).

Remington's Pharmaceutical Sciences, 18th Ed., A.R. Gennaro, Ed., Mack Publishing Co., pp. 1519–1712 (1990).

Alan Riley, "Oral Treatments for Erectile Dysfunction", *International Journal of STD & AIDS,* vol. 7, Suppl 3, pp. 16–18 (1996).

N.I. Romanenko et al, "Synthesis and biological activity of 3–methyl, 7– or 8–alkyl–, 7,8–dialkyl, heterocyclic, and cyclohexylaminoxanthines", *Chemical Abstracts,* 106: 95577n (1986).

Raymond C. Rosen et al, "The process of care model for evaluation and treatment of erectile dysfunction", *International Journal of Impotence Research,* vol. 11, pp. 59–74 (1999).

David P. Rotella et al, "N–3–Substituted Imidazoquinazolinones: Potent and Selective PDE5 Inhibitors as Potential Agents for Treatment of Erectile Dysfunction", *J. Med. Chem,* vol. 43, No. 7, pp. 1257–1263 (2000).

Robin M. Rudd et al, "Inhibition of Exercise–Induced Asthma by an Orally Absorbed Mast Cell Stabilizer (M & B 22,948)", *Br. J. Dis. Chest,* vol. 77, pp. 78–84 (1983).

Richard Sachse et al, "Safety, Tolerability and Pharmacokinetics of Bay 38–9456 in Patients with Erectile Dysfunction", *Journal of Urology,* vol. 163, No. 4, p. 204 (May 2000).

T. Saeki & I. Saito, "Isolation of Cyclic Nucleotide Phosphodiesterase Isozymes from Pig Aorta", *Biochemical Pharmacology,* vol. 46, No. 5, pp. 833–839 (1993).

Junichi Shimada et al, "A Convenient Synthesis of Tricyclic Purine Derivatives", *J. of Heterocyclic Chemistry,* vol. 30, pp. 241–246, (1993).

Christian G. Steif et al, "Cyclic nucleotide phosphodiesterase (PDE) isoenzymes in human cavernous smooth muscle: characterization and functional effects of PDE–inhibitors in vitro and in vivo", *International Journal of Impotence Research, Abstracts of the 1st Meeting of the European Society for Impotence Research (ESIR)* pp. 6–7 (Sep. 1995).

Christian G. Stief et al, "Preliminary Results with the Nitric Oxide Donor Linsidomine Chlorhydrate in the Treatment of Human Erectile Dysfunction", *The Journal of Urology,* vol. 148, No. 5, pp. 1437–1440 (Nov. 1992).

Christian G. Stief et al, "Preliminary report on the effect of the nitric oxide donor SIN–1 on human cavernous tissue in vivo", *World J. Urol,* vol. 9, pp. 237–239 (1991).

Christian G. Stief et al, "The Effect of the Specific Phosphodiesterase (PDE) Inhibitors on Human and Rabbit Cavernous Tissue in Vitro and in Vivo," *J. of Urology,* Am. Urological Assoc., vol. 159, pp. 1390–1393 (1998).

A. Taher et al, "Phosphodiesterase Activity in Human Cavernous Tissue and the Effect of Various Selective Inhibitors", *The Journal of Urology,* vol. 139, No. 4, p. 285 (Abstract) (Apr. 1993).

A. Taher et al, "Cyclic Nucleotide Phosphodiesterase Activity in Human Cavernous Smooth Muscle and the Effect of Various Selective Inhibitors", *Int. J. Impotence Res.,* vol. 4, Suppl. 2, p. 11 (1992).

Yoshlastu Takahashi et al, "Pharmacological Effects of Adenosine on Canine Penile Erection", *Tohoku J. Exp. Med.,* vol. 165, pp. 49–58 (1991).

Harvey C. Taub et al, "Relationship between Contraction and Relaxation in Human and Rabbit Corpus Cavernosum", *Urology,* vol. 42, No. 6, pp. 698–704 (Dec. 1993).

W. Joseph Thompson, "Cyclic Nucleotide Phosphodiesterases: Pharmacology, Biochemistry and Function", *Pharmac. Ther.,* vol. 51, pp. 13–33 (1991).

Flavio Trigo–Rocha et al, "The Role of Cyclic Adenosine Monophosphate, Cyclic Guanosine Monophosphate, Endothelium and Nonadrenergic, Noncholinergic Neurotransmission in Canine Penile Erection", *Journal of Urology,* vol. 149, No. 4, pp. 872–877 (Apr. 1993).

Flavio Trigo–Rocha et al, "Nitric oxide and cGMP: mediators of pelvic nerve–stimulated erection in dogs", *Am. J. Physiol.,* vol. 264, pp. H419–H422 (1993).

Flavio Trigo–Rocha et al, "Intracellular Mechanism of Penile Erection in Monkeys," *Neurology and Urodynamics,* vol. 13, pp. 71–80 (1994).

Flavio Trigo–Rocha et al, "The Effect of Intracavernous Injection of Potassium Channel Openers in Monkeys and Dogs," *Int. J. of Impotence Research,* Smith–Gordon, London, vol. 7, pp. 41–48 (1995).

Flavio Trigo–Rocho et al, "Sodium Nitroprusside: Physiologic Effects as a Nitric Oxide Donor in Three Species," *Int. J. of Impotence Research,* Smith–Gordon, London, vol. 7, pp. 49–56 (1995).

Michael C. Truss et al, "Role of the Nitric Oxide Donor Linsidomine Chlorhydrate (SIN–1) in the Diagnosis and Treatment of Erectile Dysfunction," *Urology,* vol. 44, No. 4, pp. 553–556 (Oct. 1994).

Subbarao Vemulapalli et al, "Antiplatelet and Antiproliferative Effects of SCH 51866, a Novel Type 1 and Type 5 Phosphodiesterase Inhibitor", *Journal of Cardiovascular Pharmacology,* vol. 28, pp. 862–869 (1996).

Richard J. Weiss, "Effects of Antihypertensive Agents on Sexual Function," *Am. Family Physician,* vol. 44, No. 6, pp. 2075–2082 (Dec. 1991).

E. Douglas Whitehead et al, "Treatment alternatives for impotence", *PGM Symposium,* vol. 88, No. 2 pp. 139–149, 152 (Aug. 1990).

Ahn, Ho–Sam, et al; Potent Tetracyclic Guanine Inhibitors of PDE1 and PDE5 Cyclic Guanosine Monophosphate Phosphodiesterases with Oral Antihypertensive Activity, Journal of Medicinal Chemistry, vol. 40 (1997), pp. 2196–2210.

* cited by examiner

POLYCYCLIC GUANINE DERIVATIVE PHOSPHODIESTERASE V INHIBITORS

CROSS-REFERENCE TO RELATED APPLICATION

This application claims the benefit of priority from U.S. Provisional Patent Application Ser. No. 60/344,498, filed Nov. 9, 2001, incorporated herein by reference.

BACKGROUND OF THE INVENTION

1. Field of the Invention

The invention relates to polycyclic guanine derivatives that can be useful as phosphodiesterase V inhibitors and/or for treating urological, vascular or pulmonary disorders.

2. Description

Phosphodiesterase ("PDE") V inhibitor compounds inhibit the PDE V isoenzyme. Certain xanthine/guanine PDE V inhibitors are useful for treating cardiovascular and pulmonary disorders. For example, U.S. Pat. Nos. 5,824,683, 5,939,419 and 5,393,755, each incorporated herein by reference, disclose polycyclic guanine PDE V derivatives that are useful for the treatment of cardiovascular and pulmonary disorders.

Other PDE V inhibitors are useful for treating impotence. Erectile dysfunction or impotence is a treatable and highly recognized health concern, affecting more than 30 million men in the United States, including one in four over age 65. Erectile dysfunction occurs when a man consistently is unable to sustain an erection sufficient for conducting sexual intercourse. In the past, psychological reasons were the most common explanation for erectile dysfunction or it was considered a natural part of aging. Researchers today, however, acknowledge that more than 70 percent of instances of erectile dysfunction are due to physical or medical problems. There are several factors that may contribute to erectile dysfunction, including:

Poor blood circulation due to atherosclerosis or hardening of the arteries, high blood pressure and high cholesterol;

Neurological disorders such as multiple sclerosis, Alzheimer's disease or Parkinson's disease;

Hormone imbalances due to diabetes, thyroid disorders or low testosterone levels;

Trauma caused by spinal cord injury, prostate surgery or other trauma to the pelvic area;

Prescription and over-the-counter medications such as blood pressure medications, antidepressants or certain drug combinations; or Lifestyle habits such as smoking, alcohol abuse or using illegal drugs.

One group of PDE V inhibitors described by K. Murray in *Phosphodiesterase $V_A$ Inhibitors, DN & P* 6(3), 150–156 (April, 1993), (incorporated herein by reference) has potential therapeutic value for a number of physiological disorders. One compound disclosed in the Murray article is MIMAX, a polycyclic xanthine PDE V inhibitor substituted at its 8-position with a —$NHCH_3$ group.

U.S. Pat. Nos. 5,409,934, 5,470,579, WO 93/23401, WO 92/05176 and WO 92/05175, each incorporated herein by reference, disclose certain xanthine PDE V inhibitors that are substituted at the 8-position with a number of different functionalities. Other heterocyclic PDE V inhibitors useful for treating impotence are disclosed in U.S. Pat. Nos. 6,140,329, 6,100,270 and WO 94/28902, each incorporated herein by reference.

The use of specific PDE V inhibitors for treating impotence has met with commercial success with the introduction of sildenafil citrate, a PDE V inhibitor commercially available as Viagra® (Pfizer, NY, N.Y.). The chemistry and use of Viagra®, including its mechanism of action in treating erectile dysfunction, are taught in EP 0 702 555 B1, incorporated herein by reference. Other PDE V inhibitors useful for treating erectile dysfunction are disclosed in WO 99/24433, incorporated herein by reference.

It would be desirable to provide a PDE V inhibitor that possesses beneficial therapeutic properties, useful pharmacological properties and good metabolic stability. It would further be desirable to provide a PDE V inhibitor that is highly potent and selective over other types of PDE inhibitors, and is effective for treating a variety of physiological symptoms and diseases in which PDE V plays a role, especially a treatment for erectile dysfunction with minimal side effects.

SUMMARY OF THE INVENTION

In one embodiment, the present invention is directed to a compound represented by the Formulae (Ia) or (Ib):

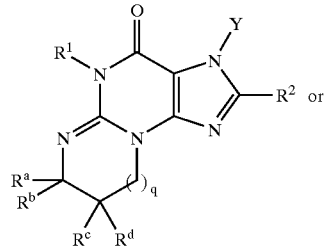

(Ia)

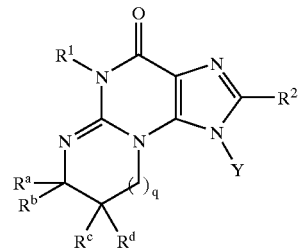

(Ib)

or a pharmaceutically-acceptable salt or solvate thereof, wherein, q=0, 1 or 2;

$R^1$, $R^a$, $R^b$, $R^c$ and $R^d$ are each independently H, alkyl, aryl, heteroaryl, cycloalkyl or heterocycloalkyl groups, wherein each alkyl group of $R^1$, $R^a$, $R^b$, $R^c$ or $R^d$ is independently unsubstituted or substituted with 1 to 5 independently selected $R^3$ moieties which can be the same or different, each $R^3$ moiety being independently selected from the group consisting of hydroxy, alkoxy, cycloalkoxy, aryloxy, alkylthio, arylthio, aryl, haloaryl, heteroaryl, cycloalkyl, heterocycloalkyl, amino, alkylamino, dialkylamino, cycloalkylamino and heterocycloalkylamino groups;

wherein each of the aryl, heteroaryl, cycloalkyl and heterocycloalkyl groups of $R^1$, $R^a$, $R^b$, $R^c$ or $R^d$ is independently unsubstituted or substituted with 1 to 5 independently selected $R^4$ moieties which can be the same or different, each $R^4$ moiety being independently selected from the group consisting of: halo, phenyl, nitro, cyano, haloalkyl, haloalkoxy, alkyl, cycloalkyl, cycloalkylalkyl, amino, alkylamino, —OCF$_3$, acyloxy, —OR$^8$, —C(O)R$^9$, —C(O)OR$^8$, —NR$^{10}$C(O)R$^9$, —NR$^{10}$C(O)OR$^8$, —NR$^{10}$S(O)$_2$R$^9$, —S(O)$_{0-2}$R$^9$ groups, carbonyl when two hydrogens attached to the same carbon atom of the cycloalkyl or heterocycloalkyl group of R$^1$ are substituted, and =CR$^8$R$^9$ when two hydrogens attached to the same carbon atom of the cycloalkyl or heterocycloalkyl groups of R$^1$ are substituted, wherein each of the aryl, heteroaryl, cycloalkyl and heterocycloalkyl groups of the R$^3$ and R$^4$ moieties above is independently unsubstituted or substituted with 1 to 5 independently selected R$^{12}$ moieties which can be the same or different, each R$^{12}$ moiety being independently selected from the group consisting of: halo, phenyl, nitro, cyano, haloalkyl, haloalkoxy, alkyl, cycloalkyl, cycloalkylalkyl, amino, alkylamino, —OCF$_3$, acyloxy, —OR$^8$, —C(O)R$^9$, —C(O)OR$^8$, —NR$^{10}$C(O)R$^9$, —NR$^{10}$C(O)OR$^8$, —NR$^{10}$S(O)$_2$R$^9$, —S(O)$_{0-2}$R$^9$ groups, carbonyl when two hydrogens attached to the same carbon atom of the cycloalkyl or heterocycloalkyl group of R$^3$ or R$^4$ are substituted, and =CR$^8$R$^9$ when two hydrogens attached to the same carbon atom of the cycloalkyl or heterocycloalkyl group of R$^3$ or R$^4$ are substituted; or R$^a$ and R$^b$, together with the carbon to which they are both attached, form a 4- to 7-membered cycloalkyl or heterocycloalkyl ring, and R$^c$ and R$^d$ are each independently H or an alkyl group; or R$^a$ and R$^c$, together with the respective carbons to which they are attached, form a 4- to 7-membered cycloalkyl or heterocycloalkyl ring, and R$^b$ and R$^d$ are each independently H or an alkyl group;

R$^2$ is H, halo, alkyl, alkoxy, alkylthio, amino, aminosulfonyl, monoalkylamino, dialkylamino, hydroxyalkylamino, aminoalkylamino, carboxy, alkoxycarbonyl, aminocarbonyl or alkylaminocarbonyl group,
  wherein each alkyl group of R$^2$ is independently unsubstituted or substituted with 1 to 5 independently selected R$^{13}$ moieties which can be the same or different, each R$^{13}$ moiety being independently selected from the group consisting of hydroxy, alkoxy, aryl, amino, monoalkylamino or dialkylamino group,
  wherein each aryl group of R$^{13}$ is independently unsubstituted or substituted with 1 to 5 independently selected R$^4$ moieties which can be the same or different;

Y is an alkyl group substituted with (i) an aryl, heteroaryl, cycloalkyl, hydroxy, alkoxy, amino, monoalkylamino or dialkylamino group, or (ii) an aryl group substituted with from one to three moieties each independently selected from the group consisting of: halo, alkyl, phenyl, hydroxy, alkoxy, phenoxy, amino, monoalkylamino and dialkylamino group;

each R$^8$ is independently H, alkyl or aryl;

each R$^9$ is independently H, alkyl, aryl or —NR$^{10}$OR$^{11}$;

each R$^{10}$ is independently H, alkyl, aryl, heteroaryl, arylalkyl or heteroarylalkyl, wherein each alkyl, aryl, heteroaryl, arylalkyl or heteroarylalkyl of R$^{10}$ is unsubstituted or independently substituted with 1 to 5 R$^{14}$ moieties which can be the same or different, each R$^{14}$ moiety being independently selected from the group consisting of: halo, alkyl, aryl, cycloalkyl, —CF$_3$, —OCF$_3$, —CN, —OR$^8$, —CH$_2$OR$^8$, —C(O)OR$^8$ and —C(O)NR$^8$R$^8$; and each R$^{11}$ is independently H, alkyl, aryl, heteroaryl, arylalkyl or heteroarylalkyl, wherein each alkyl, aryl, heteroaryl, arylalkyl or heteroarylalkyl of R$^{11}$ is unsubstituted or independently substituted with 1 to 5 R$^{14}$ moieties which can be the same or different.

Pharmaceutical compositions and methods for the treatment or prevention of urogenital, cardiovascular, cerebrovascular, peripheral vascular, angina pectoris, hypertension, post-angioplasty restenosis, endarterectomy, stent introduction, cerebral stroke, respiratory tract, allergic conditions associated with atony, pulmonary hypertension, ischemic heart, impaired glucose tolerance, diabetes and its related complications, insulin resistance syndrome, hyperglycemia, polycystic ovarian syndrome, glomerular, renal insufficiency, nephritis, tubular interstitial, autoimmune, glaucoma, intestinal motility, cachexia and cancer or for elevating the concentration of cGMP in plasma or tissue of a patient, comprising administering a therapeutically effective amount of the compound of Formulae Ia or Ib, salt or solvate thereof and a pharmaceutically acceptable carrier also are provided.

Other than in the operating examples or where otherwise indicated, all numbers used in the specification and claims expressing quantities of ingredients, reaction conditions, and so forth, are understood as being modified in all instances by the term "about."

DETAILED DESCRIPTION

Referring to Formulae Ia and Ib above:

In one embodiment, q is preferably 0 or 1 and more preferably q is 0.

In another embodiment, R$^1$ is preferably H or an alkyl group, more preferably a lower alkyl group such as a methyl group or an ethyl group.

Preferably, R$^a$, R$^b$, R$^c$ and/or R$^d$ are each independently H or an alkyl group substituted with a cycloalkyl, aryl or heteroaryl group. Each of the cycloalkyl, aryl and heteroaryl group substituents on the alkyl group of R$^a$, R$^b$, R$^c$ and/or R$^d$ can be independently unsubstituted or substituted with 1 to 5 independently selected R$^4$ moieties (detailed above) which can be the same or different. Preferably, three of R$^a$, R$^b$, R$^c$ and R$^d$ groups are H and the remaining one of R$^a$, R$^b$, R$^c$ and R$^d$ is a benzyl, monofluorobenzyl or isopropyl group.

In another embodiment of the invention, it is preferable that R$^a$ and R$^b$, together with the carbon to which they are both attached, form a 4- to 7-membered ring, more preferably, a 5-membered cyclopentyl ring, and R$^c$ and R$^d$ are each independently H or an alkyl group, more preferably H.

In yet another embodiment of the invention, it is preferable that R$^a$ and R$^c$, together with the respective carbons to which they are attached, form a 4- to 7-membered ring, more preferably, a 5-membered cyclopentyl ring, and R$^b$ and R$^d$ are each independently H or an alkyl group, more preferably H.

In another embodiment, R$^2$ is preferably H, halo, alkyl, alkoxy, alkylthio, amino, aminosulfonyl, monoalkylamino, dialkylamino, hydroxyalkylamino, aminoalkylamino, carboxy, alkoxycarbonyl, aminocarbonyl or alkylaminocarbonyl group. More preferably, R$^2$ is Br, Cl, I, methoxy, ethoxy, alkylthio (e.g., —SCH$_3$ or —SCH$_2$CH$_3$), alkoxycarbonyl (e.g., —C(O)OCH$_3$) or aminocarbonyl (e.g., —C(O)NH$_2$ or —C(O)NHCH$_3$) group.

In another embodiment, Y is preferably an alkyl group substituted with (ii) an aryl group substituted with from one to three moieties each independently selected from the group consisting of: halo, alkyl, phenyl, hydroxy, alkoxy, phenoxy, amino, monoalkylamino and dialkylamino group. More preferably, Y is:

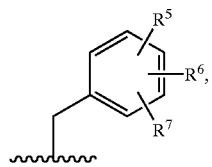

wherein, $R^5$, $R^6$ and $R^7$ are each independently selected from the group consisting of: H, halo, alkyl (e.g., —$CH_3$), hydroxy and alkoxy. More preferably, Y is a benzyl group substituted with from one to two substituents selected from the group consisting of: bromo, chloro, alkyl, hydroxy and alkoxy.

Non-limiting examples of suitable compounds of Formulae Ia and Ib are shown below in Table I. Methods for making each of these compounds are described in the corresponding Examples below.

TABLE I

| Example Number | Structure |
| --- | --- |
| 1 | |
| 1.3.2 | |
| 2 | 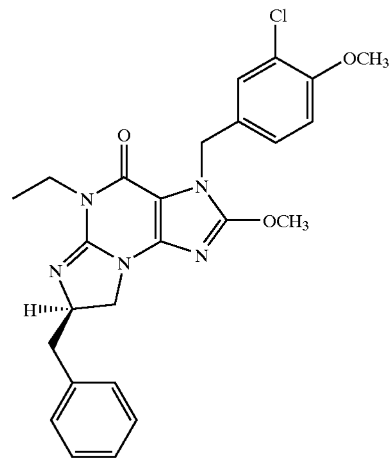 |
| 3 | 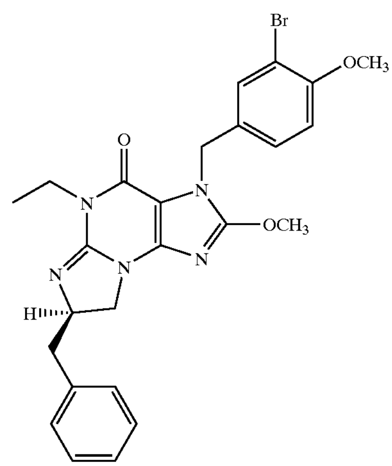 |
| 4 | 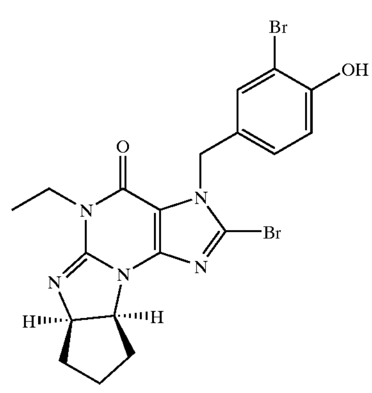 |

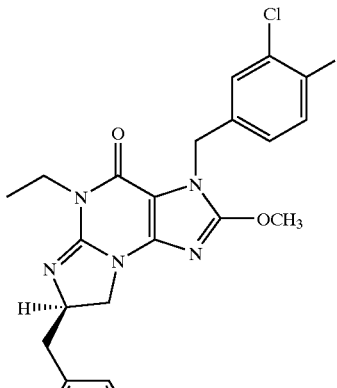

TABLE I-continued
| Example Number | Structure |
|---|---|
| 5 | 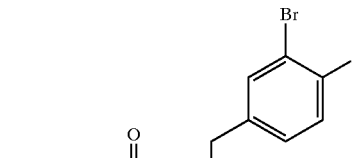 |
| 6 | 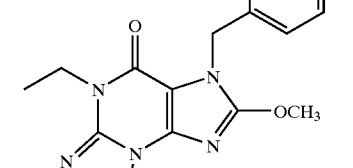 |
| 7 | 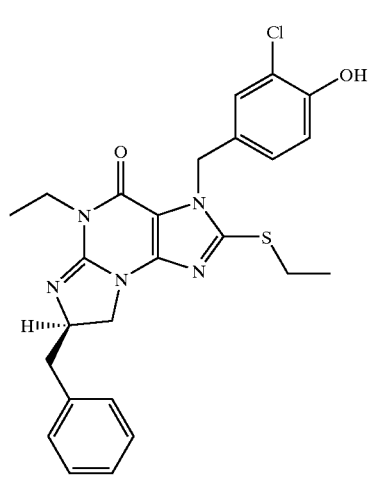 |
TABLE I-continued
| Example Number | Structure |
|---|---|
| 8 | 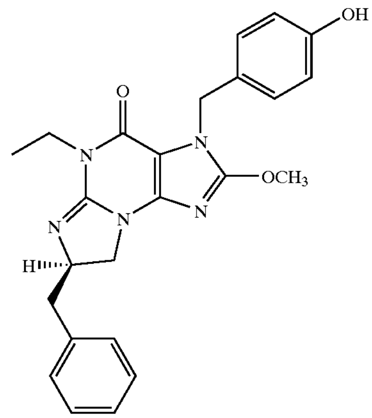 |
| 9 | 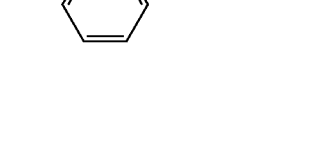 |
| 10 | 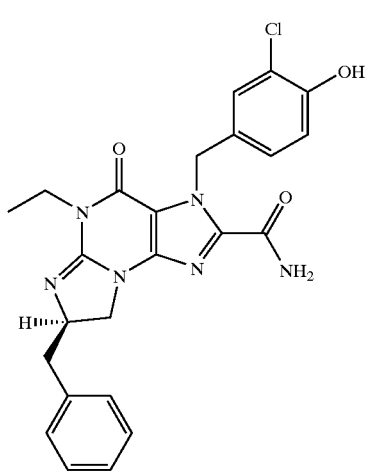 |

TABLE I-continued
| Example Number | Structure |
|---|---|
| 11 | 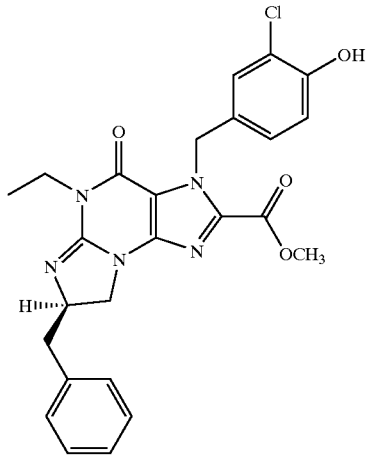 |
| 12 | 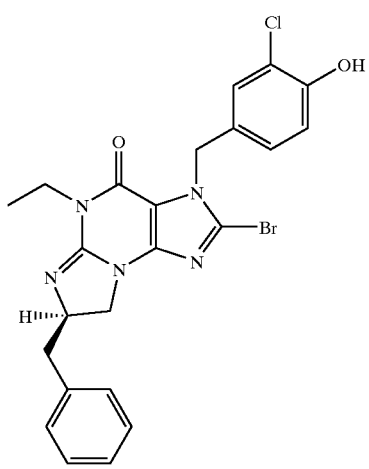 |
| 13 | 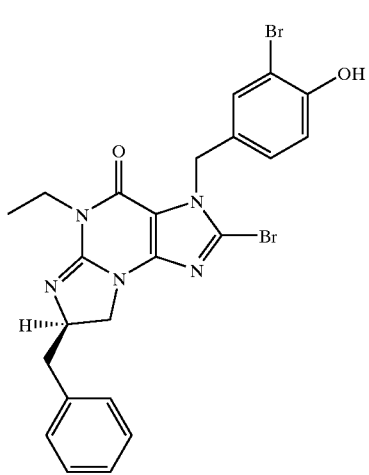 |
| 14 | 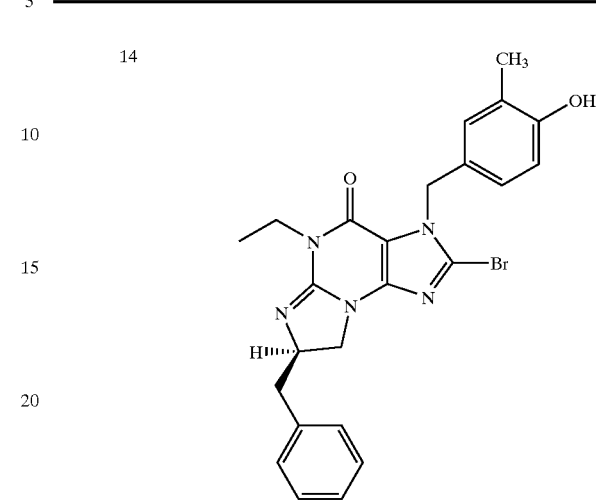 |
| 15 | 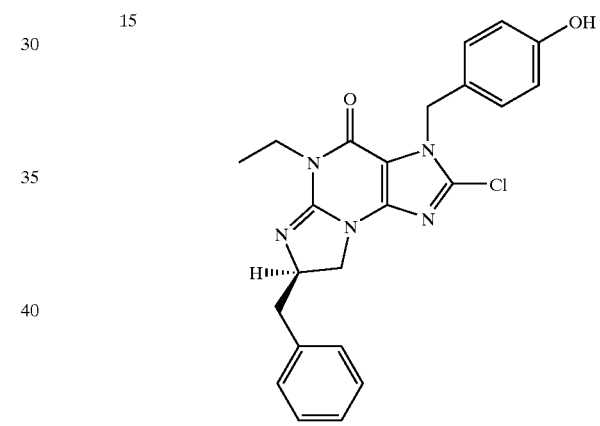 |
| 16 | 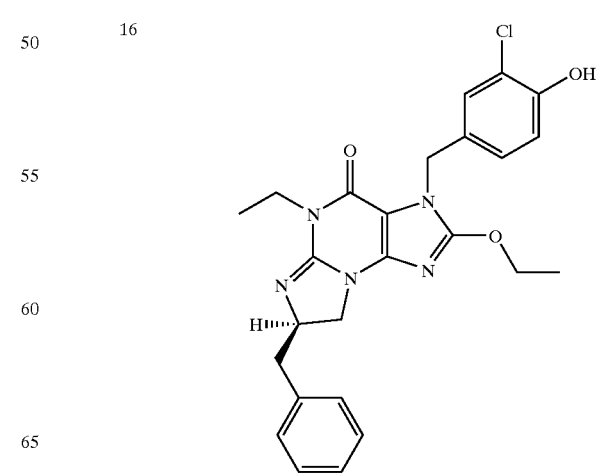 |

TABLE I-continued
| Example Number | Structure |
|---|---|
| 17 | 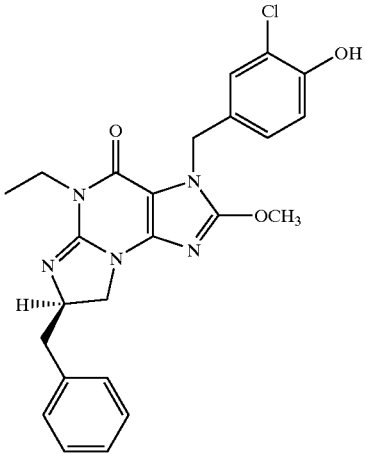 |
| 18 | 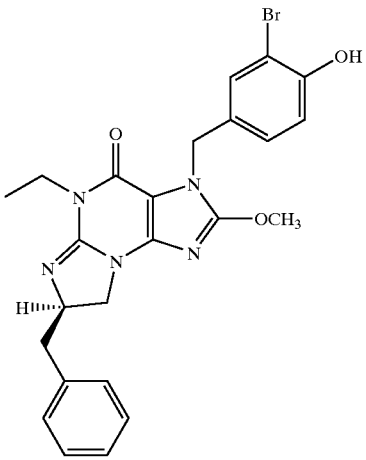 |
| 19 | 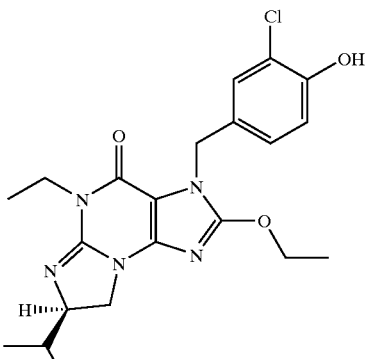 |
| 20 | 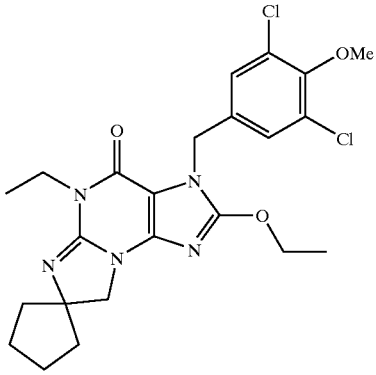 |
| 21 | 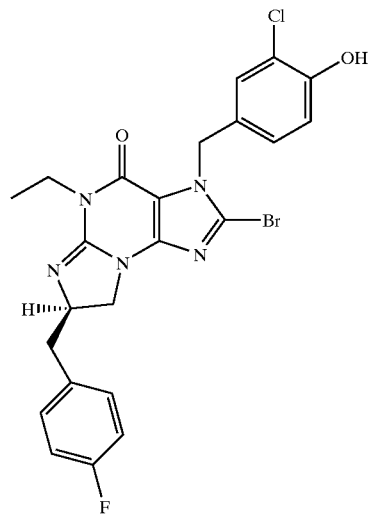 |
| 22 | 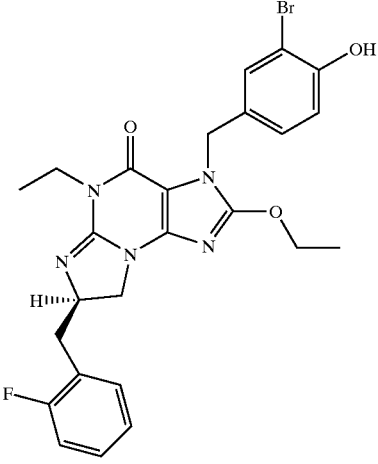 |

TABLE I-continued

| Example Number | Structure |
|---|---|
| 23 | (structure: 8-bromo, N-ethyl, N'-(3-bromo-4-hydroxybenzyl), fused imidazoline with 3-fluorobenzyl substituent) |
| 24 | (structure: 8-ethoxy, N-ethyl, N'-(3-bromo-4-methoxybenzyl), fused imidazoline with 3-fluorobenzyl substituent) |
| 25 | (structure: 8-chloro, N-ethyl, N'-(3-hydroxybenzyl), spiro-cyclopentane imidazoline) |
| 26 | (structure: 8-iodo, N-ethyl, N'-(3-hydroxybenzyl), spiro-cyclopentane imidazoline) |
| 27 | (structure: 8-chloro, N-ethyl, N'-(4-hydroxybenzyl), spiro-cyclopentane imidazoline) |

In one embodiment, preferred compounds of the invention include Compound Nos. 1, 2, 3, 5, 6, 8, 10, 11, 16–18, 22 and 24 above. More preferred compounds of the invention include Compound Nos. 1, 2, 5, 10, 11 and 16–18. Even more preferred compounds of the invention include Compound Nos. 2, 5, 11 and 16–18.

As used above and throughout this disclosure, the following terms, unless otherwise indicated, shall be understood to have the following meanings:

"Patient" means both humans and animals, preferably humans.

"Mammal" means humans and other mammalian animals.

Chemical names, common names, and chemical structures may be used interchangeably to describe the same structure. These definitions apply regardless of whether a term is used by itself or in combination with other terms, unless otherwise indicated. Therefore, the definition of "alkyl" applies to "alkyl" as well as the "alkyl" portions of "hydroxyalkyl," "haloalkyl," "alkoxy," etc.

Unless otherwise known, stated or shown to be to the contrary, the point of attachment for a multiple term substituent (multiple terms that are combined to identify a single moiety) to a subject structure is through the last named term of the multiple term. For example, an "arylalkyl" substituent attaches to a structure through the "alkyl" portion of the substituent. Conversely, when the substituent is "alkylaryl", it attaches to a structure through the "aryl" portion of the substituent.

When a variable appears more than once in a structural formula (e.g., $R^8$ appears twice in —C(O)NR$^8$R$^8$), the identity of each variable appearing more than once may be independently selected from the definition for that variable.

The term "substituted," as used herein, means the replacement of one or more atoms or radicals, usually hydrogen, in a given structure with a selected atom(s) or radical(s) ("substituent"). In the situations where more than one atom or radical may be replaced with a substituent selected from the same specified group, the substituents may be, unless otherwise specified, either the same or different at each position.

It should also be noted that any heteroatom with unsatisfied valences in the text, schemes, examples and Tables herein is assumed to have the hydrogen atom to satisfy the valences.

As used herein, the term "alkyl" means an aliphatic hydrocarbon group that can be straight or branched and comprising 1 to about 20 carbon atoms in the chain. Preferred alkyl groups comprise 1 to about 12 carbon atoms in the chain. More preferred alkyl groups comprise 1 to about 6 carbon atoms in the chain, most preferably 1 to about 3 carbon atoms in the chain. "Branched" means that one or more lower alkyl groups, such as methyl, ethyl or propyl, are attached to a linear alkyl chain. "Lower alkyl" means a group having about 1 to about 6 carbon atoms in a chain that may be straight or branched. Suitable alkyl substituents are discussed in detail above. Where an alkyl chain joins two other variables and is therefore bivalent, the term alkylene is used.

"Alkoxy" means an alkyl-O— group in which the alkyl group is as previously described. Useful alkoxy groups can comprise 1 to about 12 carbon atoms, preferably 1 to about 6 carbon atoms. Non-limiting examples of suitable alkoxy groups include methoxy, ethoxy and isopropoxy. The alkyl group of the alkoxy is linked to an adjacent moiety through the ether oxygen.

"Alkylthio" means an alkyl-S— group in which the alkyl group is as previously described. Non-limiting examples of suitable alkylthio or alkylsulfanyl groups include methylthio, ethylthio and isopropylthio. The alkyl is linked to an adjacent moiety through the sulfur.

"Amino" means an —$NH_2$ group.

"Cycloalkylamino" means an amino group in which the hydrogen is substituted with a cycloalkyl group as described below. The cycloalkyl is linked to an adjacent moiety through the amino residue. Similarly, a "heterocycloalkylamino" means an amino group in which the hydrogen is substituted with a heterocycloalkyl group as described below.

"Alkylamino" means an amino group in which one of the hydrogens is substituted with an alkyl group. "Dialkylamino" means an amino group in which two of the hydrogens are substituted with alkyl groups. Preferred groups are those in which the alkyl group(s) is lower alkyl. The alkyl(s) is linked to an adjacent moiety through the amino residue.

"Aryl" means an aromatic monocyclic or multicyclic ring system comprising about 5 to about 14 carbon atoms, preferably about 6 to about 10 carbon atoms. The aryl group can be substituted with one or more "ring system substituents" which may be the same or different, and are as defined herein. Non-limiting examples of suitable aryl groups include phenyl, naphthyl, indenyl, tetrahydronaphthyl and indanyl. "Phenylene" means a bivalent phenyl group, including ortho, meta and para-substitution.

"Aryloxy" means an aryl-O— group in which the aryl group is as previously described. Useful aryloxy groups can comprise 5 to about 14 carbon atoms, preferably 6 to about 10 carbon atoms. A non-limiting example of a suitable aryloxy group is phenoxy. The aryl group of the aryloxy is linked to an adjacent moiety through the ether oxygen.

"Arylthio" means an aryl-S— group in which the aryl group is as previously described. A non-limiting example of a suitable arylthio group is phenylthio. The aryl is linked to an adjacent moiety through the sulfur.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, phenethyl and naphthlenylmethyl. The aralkyl is linked to an adjacent moiety through the alkyl group.

"Carbonyl" means a radical having a carbon to oxygen double bond, (e.g., —C(=O)—).

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be substituted with one or more "ring system substituents" which may be the same or different, and are as defined below. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornyl, adamantyl and the like. "Cycloalkylene" refers to a corresponding bivalent ring, wherein the points of attachment to other groups include all positional isomers.

"Cycloalkoxy" means a cycloalkyl-O— group in which the cycloalkyl group is as previously described. Useful cycloalkoxy groups can comprise 3 to about 10 carbon atoms, preferably 5 to about 7 carbon atoms. Non-limiting examples of suitable cycloalkoxy groups include cyclohexyloxy and cyclopentyloxy. The cycloalkyl group of the cycloalkoxy is linked to an adjacent moiety through the ether oxygen.

"Halo" refers to fluorine, chlorine, bromine or iodine radicals. Preferred are fluoro, chloro or bromo, and more preferred are fluoro and chloro.

"Haloaryl" means a halo-substituted aryl group in which the halo atom(s) and aryl are as previously described. Non-limiting examples of suitable haloaryl groups include fluoroaryl or chloroaryl. The halo is linked to an adjacent moiety through the aryl.

"Heteroaryl" means a monocyclic or multicyclic aromatic ring system of about 5 to about 14 ring atoms, preferably about 5 to about 10 ring atoms, in which one or more of the atoms in the ring system is/are atoms other than carbon, for example nitrogen, oxygen or sulfur. The heteroatom(s) interrupt a carbocyclic ring structure and have a sufficient number of delocalized pi electrons to provide aromatic character, provided that the rings do not contain adjacent oxygen and/or sulfur atoms. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be oxidized to form the corresponding N-oxide. All regioisomers are contemplated, e.g., 2-pyridyl, 3-pyridyl and 4-pyridyl. Examples of useful 6-membered heteroaryl groups include pyridyl, pyrimidinyl, pyrazinyl, pyridazinyl and the like and the N-oxides thereof. Examples of useful 5-membered heteroaryl rings include furyl, thienyl, pyrrolyl, thiazolyl, isothiazolyl, imidazolyl, pyrazolyl and isoxazolyl. Useful bicyclic groups are benzo-fused ring systems derived from the heteroaryl groups named above, e.g., quinolyl, phthalazinyl, quinazolinyl, benzofuranyl, benzothienyl and indolyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocycloalkyls contain about 5 to about 6 ring atoms. The prefix aza, oxa or thia before the heterocycloalkyl root name means that at least a nitrogen, oxygen or sulfur atom respectively is present as a ring atom. The heterocycloalkyl can be optionally substituted by one or more ring system substituents as described above. The nitrogen or sulfur atom of the heterocycloalkyl optionally can be oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

"Ring system substituent" means a substituent attached to an aromatic or non-aromatic ring system which, for example, replaces an available hydrogen on the ring system. Ring system substituents may be the same or different. Suitable ring system substituents for the aryl, heteroaryl, cycloalkyl and heterocycloalkyl group(s) of $R^1$, $R^a$, $R^b$, $R^c$ and $R^d$ and the aryl group(s) of $R^{13}$ are 1 to 5 independently selected $R^4$ moieties as discussed above. Each of the aryl, heteroaryl, cycloalkyl and heterocycloalkyl $R^4$ moieties can be substituted with 1 to 5 independently selected $R^{12}$ moieties as discussed above. The aryl group (ii) of Y can be substituted with one to three ring system substituents or moieties each independently selected from the group consisting of halo, alkyl, phenyl, hydroxy, alkoxy, phenoxy, amino, monoalkylamino and dialkylamino groups.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, N.Y.

When any variable (e.g., aryl, heterocycloalkyl, $R^3$, etc.) occurs more than one time in any constituent or in Formulae Ia or Ib, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formulae Ia or Ib or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formulae Ia and Ib can form salts that are also within the scope of this invention. Reference to a compound of Formulae Ia or Ib herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formulae Ia or Ib contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of Formulae Ia or Ib may be formed, for example, by reacting a compound of Formulae Ia or Ib with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formulae Ia and Ib, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The compounds of the invention can be useful for inhibiting PDE V isoenzymes. Isoenzyme activity (potency) and isoenzyme selectivity for a compound can be evaluated in a number of ways. For instance, enzyme activity (potency) can be measured by a PDE V $IC_{50}$ value, which is the concentration (in nM) of compound required to provide 50% inhibition of PDE V isoenzyme. The lower the value of PDE V $IC_{50}$, the more active (potent) is the compound to inhibiting the PDE V isoenzyme. Similarly, an $IC_{50}$ value may be obtained for other PDE isoenzymes, such as the PDE VI isoenzyme. Isoenzyme selectivity in this respect may be defined as the activity (potency) of a PDE inhibitor compound for a particular PDE isoenzyme as opposed to another PDE isoenzyme, for example, the activity of a compound to inhibit a PDE V isoenzyme compared to the activity of the same compound to inhibit a PDE VI isoenzyme. Once the PDE V $IC_{50}$ and PDE VI $IC_{50}$ values have been measured, one can calculate a selection ratio of PDE VI $IC_{50}$/PDE V $IC_{50}$, which is an indicator of isoenzyme selectivity—the larger the selection ratio, the more selective is the compound to inhibiting PDE V isoenzyme relative to PDE VI isoenzyme.

Potent compounds of the invention generally have a PDE V $IC_{50}$ of between about >0 nM and about 22 nM, preferably, between about 0.1 nM and about 7 nM, more preferably, between about 0.4 nM and about 5 nM, even more preferably, between about 0.7 nM and 3 nM. These compounds are relatively highly potent (active) for inhibiting the PDE V isoenzyme. The compounds of the invention generally have a PDE VI $IC_{50}$ of > about 50 nM, preferably, between about 100 nM and about 2,500 nM, more preferably, between about 200 nM and about 1,900 nM, and even more preferably, between about 400 nM and about 1,400 nM. These compounds exhibit relatively low potency (activity) for inhibiting the PDE VI isoenzyme. Selective compounds of the invention generally have a selection ratio of PDE VI $IC_{50}$/PDE V $IC_{50}$ of > about 50, preferably, between about 50 and about 1,000, more preferably, between about 100 and about 850, and even more preferably, between about 200 and about 700. Looking at all three properties (PDE V $IC_{50}$, PDE VI $IC_{50}$ and ratio of PDE VI $IC_{50}$/PDE V $IC_{50}$), the compounds of the invention preferably have a PDE V $IC_{50}$ of between about >0 nM and about 7 nM, a PDE VI $IC_{50}$ of between about 100 nM and about 2,000 nM, and a selection ratio of PDE VI $IC_{50}$/PDE V $IC_{50}$ of between about 75 and about 1,000. More preferred compounds possess a combination of higher potency (as measured by PDE V $IC_{50}$) and/or higher selectivity (as measured by a ratio of PDE VI $IC_{50}$/PDE V $IC_{50}$), as described above.

The compounds illustrated in Table I exhibited the following properties:

PDE V $IC_{50}$

Compounds 1, 1.3.2, 2–6, 8–13, 15–19 and 21–23: a PDE V $IC_{50}$ of about <4.1 nM.

Compounds 1, 2–6, 8, 11, 15–18 and 21: a PDE V $IC_{50}$ of about <2.5 nM.

Compounds 2, 4, 5, 11 and 16–18: a PDE V $IC_{50}$ of about <1.6 nM.

PDE VI $IC_{50}$

Compounds 1, 1.3.2, 2, 3, 5, 7–14 and 16–27: a PDE VI $IC_{50}$ of about >300 nM.

Compounds 1, 7, 10, 12–14, 16–18, 20 and 23–27: a PDE VI $IC_{50}$ of about >475 nM.

Compounds 7, 10, 12–14, 20, 23 and 25–27: a PDE VI $IC_{50}$ of about >875 nM.

Ratio of PDE VI $IC_{50}$/PDE V $IC_{50}$

Compounds 1, 1.3.2, 2–13 and 15–27: a ratio of PDE VI $IC_{50}$/PDE V $IC_{50}$ of about >90.

Compounds 1, 2, 5, 10–13, 16–18, 21 and 23: a ratio of PDE VI $IC_{50}$ I PDE V $IC_{50}$ of about >195.

Compounds 10, 13 and 16–18: a ratio of PDE VI $IC_{50}$/PDE V $IC_{50}$ of about >440.

Combination of PDE V $IC_{50}$, PDE VI $IC_{50}$ and Ratio of PDE VI $IC_{50}$/PDE V $IC_{50}$ Compounds 1, 1.3.2 and 2–27: a PDE V $IC_{50}$ of about <22 nM, a PDE VI $IC_{50}$ of about >125 nM, and a ratio of PDE VI $IC_{50}$/PDE V $IC_{50}$ of about >70.

Compounds 1, 1.3.2, 2, 3, 5, 8–13, 16–19, 22 and 23: a PDE V $IC_{50}$ of about <4.1 nM, a PDE VI $IC_{50}$ of about >300 nM, and a ratio of PDE VI $IC_{50}$/PDE V $IC_{50}$ of about >90.

Compounds 1, 2, 5, 11, 16–19 and 21: a PDE V $IC_{50}$ of about <2.2 nM, a PDE VI $IC_{50}$ of about >325 nM, and a ratio of PDE VI $IC_{50}$/PDE V $IC_{50}$ of about >195.

As shown by the data, compounds having the Formulae (Ia) and (Ib) are potent (as measured by PDE V $IC_{50}$) and selective (as measured by PDE VI $IC_{50}$/PDE V $IC_{50}$) PDE V isoenzyme inhibitors.

The compounds of Formulae (Ia) and (Ib) exhibited unexpectedly favorable properties with respect to PDE V isoenzyme activity and selectivity, which means they may be particularly useful for treating urogenital diseases, such as male and female sexual dysfunction, particularly erectile dysfunction. The resulting compositions may be administered in vivo to patients or mammals, such as men or women, to treat a variety of disease states (disorders, symptoms and diseases). For example, the inventive compounds and compositions may be used to treat diseases of the urogenital system, specifically, male erectile dysfunction (e.g., impotence) and female sexual dysfunction. Male erectile dysfunction may be defined as an inability of a male to sufficiently obtain, achieve and/or sustain a penile erection adequate to have intercourse with his mate. In the treatment of erectile dysfunction, it is believed that the compounds of Formulae (Ia) and (Ib) can be useful therapeutic agents because they can elevate cGMP (cyclic guanosine monophosphate) levels in the human body. Such an action may facilitate corpus cavernosum smooth muscle relaxation, which would provide an increased flow of blood therein, resulting in an erection. This makes the inventive compounds especially useful for treating erectile dysfunction and other types of diseases that are ameliorated by elevation of cGMP levels, such as ischemic heart disease, pulmonary hypertension, hypertension, complications of diabetes resulting from poor circulation, esophageal disorders and anal fissures. The level of cGMP in the plasma or tissue of a patient can be determined by radioimmunoassay using methods well known to those skilled in the art (for example, G. Brooker, J. F. Harper, W. L. Terasaki, and R. D. Moylan, Adv. Cyclic Nucleotide Res. 10, 1 (1979)) or by using a commercially available radioimmunoassay kit such as RPA541 which is available from Amersham of Little Chalfont, Buckinghamshire, England (2000).

Accordingly, another aspect of the invention is a method for treating erectile dysfunction in a patient in need of such treatment, comprising administering to the patient at least one compound having the Formulae (Ia) or (Ib), a pharmaceutically-acceptable salt or solvate thereof, or a pharmaceutical composition comprising the same, in an amount effective to ameliorate and/or reduce one or more of the symptoms associated with erectile dysfunction sufficiently enough so that the patient can conduct and complete intercourse with another subject.

The most commonly prescribed medication to treat physiologically-caused erectile dysfunction ("ED"), Viagra® (sildenafil citrate), can cause certain patients to experience undesirable side effects. For instance, the use of Viagra® is contraindicated for patients who are using organic nitrates, either regularly or intermittently. *Physicians' Desk Reference®*, 55$^{th}$ Ed, pp. 2534–37 (2001). Combining Viagra® with nitrates can cause a hypotensive episode or suddenly reduce blood pressure to dangerous levels, which may cause a heart attack. Id. Accordingly, men who have a heart condition that requires the use of nitrate drugs are advised not use Viagra®. Id. It has also been reported that Viagra® can cause a vision side effect by impairing the patient's color discrimination (blue/green), causing a "blue-halo" light visual alteration. Id. This side effect is believed to be due to inhibition of the PDE VI isoenzyme (found in a retina). Id.

An advantage of the inventive compounds is that they can be particularly selective for the PDE V isoenzyme in comparison to other types of PDE isoenzymes, such as the PDE VI isoenzyme. It is believed that this increased selectivity will ameliorate side effects associated with the use of Viagra®. In particular, the high selectivity of the inventive compounds should minimize, and may even prevent, the occurrence of a "blue-halo" light visual alteration. The increased isoenzyme selectivity in inhibiting PDE V isoenzyme (found in a penis) versus PDE VI isoenzyme (found in a retina) can reduce or eliminate the "blue-halo" visual side effect.

Furthermore, the inventive compounds can reduce or eliminate adverse reactions with nitrate medication in a rat. Nitrates, such as nitroglycerin, isosorbide dinitrate or isosorbide 5-mono-nitrate, are commonly used to treat cardiovascular conditions. An adverse reaction with nitrate medication may be dangerous and fatal. Adverse reactions include any reaction that could jeopardize or otherwise diminish the body's physiological functions. More specifically, in the case of a combination therapy for a patient, comprising administering to the patient a nitrate donating agent and a PDE V inhibitor agent (separately or together), an adverse nitrate reaction would be one in which the patient's blood pressure drops significantly more than with either agent administered alone.

This lack of adverse nitrate interaction would allow for a method of erectile dysfunction treatment to many patients who suffer from both an erectile dysfunction and a cardiovascular or other disease(s) that is treated with a nitrate donating medicament. Patients suffering from two or more different ailments that require dual (or multiple) treatments may have been born with one or both ailments, or later developed one or both ailments due to genetics or some other type of injury or disease, such as nerve damage, spinal cord injury, diabetes, and the like. It is another embodiment of this invention to treat a patient suffering from both (1) an erectile dysfunction and (2) at least one condition that can be treated with a nitrate donor medication, the inventive treatment comprising a combination therapy comprising an administration to a mammal of at least one inventive compound, or a pharmaceutically-acceptable salt or solvate thereof, or a pharmaceutical composition comprising the same, and at least one nitrate donating compound or a pharmaceutical composition thereof. The patient suffering from both an erectile dysfunction and a need for a nitrate donating medicament can be treated for both conditions in a variety of conventional ways, such as by simultaneous administration of the compound(s) of Formulae Ia or Ib and a nitrate donor medication, consecutively (one after the other within a relatively short period of time), or sequentially (first one and then the other over a period of time). The combination therapy can be taken separately in any form, preferably, in oral or patch doses, or can be formulated together for a single, combined dosage.

The compounds of the invention may be employed alone or in combination with other active agents, for example, other types of PDE inhibitors (such as UK-357903 or UK-369003 (Pfizer)), TA-1790 (Tanabe), DA-8159 (Dong-A), E-4010 or E-8010 (Eisai), BMS-341400 (Bristol Myers Squibb), LAS-34837 and LAS-34179 (Almarill Prodesfarma), and other cGMP PDE V inhibitors which are chemically different from those compounds of Formulae Ia or Ib), prostanoids, α-adrenergic receptor antagonists, dopamine receptor agonists, melanocortin receptor agonists, endothelin receptor antagonists, endothelin converting enzyme inhibitors, angiotensin 11 receptor antagonists, angiotensin converting enzyme inhibitors, neutral metalloendopeptidase inhibitors, renin inhibitors, serotonin 5-HT$_{2c}$ receptor agonists, nociceptin receptor agonists, rho kinase inhibitors, potassium channel modulators and inhibitors of multidrug resistance protein 5. Examples of therapeutic agents that may be used in combination with compounds of the invention are the following: other types of PDE V inhibitors, such as sildenafil citrate (Viagra®, Pfizer, Connecticut, United States), Vardenafil™ (Bayer, Germany) and IC-351 (Cialis™, Lilly-ICOS, Washington and Indiana, United States); prostanoids, such as prostaglandin E$_1$; α-adrenergic agonists, such as phentolamine mesylate; dopamine receptor agonists, such as apomorphine; angiotensin II antagonists, such as losartan, irbesartan, valsartan and candesartan; and ET$_A$ antagonists, such as bosentan and ABT-627.

It is understood that combinations other than those described above may be undertaken with routine experimentation by one of ordinary skill in the art to treat mammalian disease states, while remaining within the scope of the invention. While any of the inventive compounds may be used in an application of monotherapy to a patient, they also may be used in combination therapy, in which one or more of the inventive compounds are combined with one another or with one or more other pharmaceutical compounds. The combination therapy is useful for treating a variety of disorders, symptoms and diseases, such as one or more of the mammalian disease states described above.

As discussed above, due to their cGMP-PDE V inhibitory activities, the inventive compounds are useful for treating urological disorders, in particular, female and male sexual dysfunctions such as erectile dysfunction and premature ejaculation. Other physiological disorders, symptoms and diseases can also benefit from cGMP-PDE V inhibition. More specifically, the inventive compounds, salts, etc., and pharmaceutical compositions thereof, may be used to treat cardiovascular and cerebrovascular diseases, angina pectoris, hypertension, restenosis post angioplasty, endarterectomy, stent introduction, peripheral vascular diseases, cerebral stroke, respiratory tract disorders, such as reversible airway obstruction, chronic asthma and bronchitis, allergic disorders associated with atony, such as urticaria, eczema, and rhinitis, pulmonary hypertension, ischemic heart diseases, impaired glucose tolerance, diabetes and related complications, insulin resistance syndrome, hyperglycemia, polycystic ovarian syndrome, glomerular diseases, renal insufficiency, nephritis, tubular interstitial disease, autoimmune diseases, glaucoma, intestinal motility disorders, cachexia cancer, neuropathy, cognitive impairment, esophageal disorders such as nutcracker esophagus, and anal fissures.

Another aspect of the invention is to provide a kit comprising separate containers in a single package, wherein inventive pharmaceutical compounds, salts, solvates and/or compositions are used in combination with pharmaceutically-acceptable carriers to treat physiological disorders, symptoms and diseases where cGMP-PDE V inhibition plays a role.

Pharmaceutically-Acceptable Dosage Forms

The compounds and compositions of the present invention can be administered to a patient in need of such treatment in a therapeutically effective amount to treat any of the conditions discussed above, such as vascular, pulmonary or urological conditions. The compounds and compositions can be administered by any suitable means that produce contact of these compounds with the site of action in the body, for example in the plasma or vascular smooth muscle of a patient.

The phrases "effective amount" and "therapeutically effective amount" mean that amount of a compound of Formula Ia and/or Ib, and other pharmacological or therapeutic agents described below, that will elicit a biological or medical response of a tissue, system, or patient that is being sought by the administrator (such as a researcher, doctor or veterinarian) which includes alleviation of the symptoms of the condition or disease being treated and the prevention, slowing or halting of progression of one or more conditions, for example vascular, pulmonary and/or urological conditions, such as erectile dysfunction. As used herein, "vascular" comprises cardiovascular, cerebrovascular, peripheral vascular and combinations thereof.

The daily dosage for the various compounds or compositions described above can be administered to a patient in a single dose or in multiple subdoses, as desired. Subdoses can be administered 2 to 6 times per day, for example. Sustained release dosages can be used. Where the inventive compounds(s) and other active agent(s) are administered in separate dosages, the number of doses of each component given per day may not necessarily be the same, e.g., one component may have a greater duration of activity and will therefore need to be administered less frequently.

Useful pharmaceutical compositions according to the present invention typically comprise from about 0.1% to about 99.9% (by weight or volume, preferably, w/w) of active ingredient (compound(s) having the Formulae (Ia) or (Ib)), preferably, from about 5% to about 95%, more preferably, from about 20% to about 80%. For preparing pharmaceutical compositions containing the inventive compounds, inert, pharmaceutically acceptable carriers can be either solid or liquid.

The compounds of the present invention may be administered to patients by a variety of routes, including oral dosage forms and injections (intravenous, intramuscular, intraperitoneal, subcutaneous, and the like). Numerous other dosage forms containing the compounds of the present invention can be readily formulated by one skilled in the art, utilizing the suitable pharmaceutical excipients as defined below. For considerations of patient compliance, oral dosage forms are generally most preferred.

The pharmaceutical treatment compositions and therapeutic combinations of the present invention can further comprise one or more pharmaceutically acceptable carriers, one or more excipients and/or one or more additives. Non-limiting examples of pharmaceutically acceptable carriers include solids and/or liquids such as ethanol, glycerol, water and the like. The amount of carrier in the treatment composition can range from about 5 to about 99 weight percent of the total weight of the treatment composition or therapeutic combination. Non-limiting examples of suitable pharmaceutically acceptable excipients and additives include non-toxic compatible fillers, binders such as starch, disintegrants, buffers, preservatives, anti-oxidants, lubricants, flavorings, thickeners, coloring agents, emulsifiers and the like. The amount of excipient or additive can range from about 0.1 to about 90 weight percent of the total weight of the treatment composition or therapeutic combination. One skilled in the art would understand that the amount of carrier(s), excipients and additives (if present) can vary.

Solid form preparations include powders, tablets, dispersible granules, capsules, cachets and suppositories. Suitable solid carriers are known in the art, for example, magnesium carbonate, magnesium stearate, talc, sugar and lactose. Tablets, powders, cachets and capsules can be used as solid dosage forms suitable for oral administration. Examples of pharmaceutically-acceptable carriers and methods of manufacture for various compositions may be found in *Remington's Pharmaceutical Sciences*, 18$^{th}$ Ed., Mack Publishing Co. (1990), which is incorporated in its entirety by reference herein.

Liquid form preparations include solutions, suspensions and emulsions. Common liquid form preparations include water and water-propylene glycol solutions for parenteral injection or addition of sweeteners and opacifiers for oral solutions, suspensions and emulsions. Liquid form preparations may also include solutions for intranasal administration.

Aerosol preparations suitable for inhalation include solutions and solids in powder form, which may be combined with a pharmaceutically acceptable carrier, such as an inert compressed gas (e.g., nitrogen).

Also included are solid form preparations that may be converted, shortly before use, to liquid form preparations for either oral or parenteral administration. Such liquid forms include solutions, suspensions and emulsions.

The compounds of the invention may also be delivered transdermally. The transdermal compositions can take the form of creams, lotions, aerosols and emulsions and may be included in a transdermal patch of a matrix or reservoir type as is conventional in the art for this purpose.

The preferred mode of administering the compounds of the invention is oral. Preferably, the pharmaceutical preparation is in a unit dosage form. In such a form, the preparation is subdivided into suitable sized unit doses containing appropriate quantities of the active component, for example, an effective amount to achieve the desired purpose.

The quantity of active ingredient (compound) in a unit dose of preparation may be varied or adjusted from about 0.01 mg to about 4,000 mg, preferably, from about 0.02 mg to about 2,000 mg, more preferably, from about 0.03 mg to about 1,000 mg, even more preferably, from about 0.04 mg to about 500 mg, and most preferably, from about 0.05 mg to about 250 mg, according to the particular application. A typical recommended daily dosage regimen for oral administration can range from about 0.02 mg to about 2,000 mg/day, in two to four divided doses. For convenience, the total daily dosage may be divided and administered in portions during the day as required.

A typical recommended daily dosage regimen for oral administration can range from about 0.01 mg/kg to about 100 mg/kg of body weight per day, preferably, between about 0.5 mg/kg and about 75 mg/kg of body weight per day, and more preferably, between about 1 mg/kg and about 50 mg/kg of body weight per day, of the inventive compounds, salts, and solvates described herein.

The compounds of Formulae Ia and Ib can provide efficacious treatment of (male) erectile dysfunction, including a reasonable time of onset upon administration, and a reasonable duration after administration. For example, in the treatment of erectile dysfunction, a dosage of the inventive compound may be taken about an hour before a sex act is to be undertaken. Particular dosages will work within about thirty minutes of their administration. Ideal dosages will affect a patient within about fifteen minutes of their administration. While food, diet, pre-existing conditions, alcohol and other systemic conditions could lengthen the time delay for an inventive drug to work after its administration, it is understood that optimum dosages in combination with sexual stimulation will result in an efficacious drug treatment within and for a reasonable amount of time.

Definitions for Abbreviations

Following are general and specific methods of preparing compounds having the formula (Ia) and (Ib). As used herein, the following abbreviations are defined as follows:

RT is room temperature;
Me is methyl;
Bu is butyl;
OH is hydroxyl;
MeOH is methanol;
Br is bromo;
Ac is acetyl;
AcOH is acetic acid;
Et is ethyl;
EtOH is ethanol;
Ph is phenyl;
THF is tetrahydrofuran;
OAc is acetate;
EtOAc is ethyl acetate;
Et$_2$O is ethyl ether;
LDA is lithium diisopropylamide;
Et$_3$N is triethylamine;
DMF is dimethylformamide;
i-Pr$_2$NEt is diisopropylethylamine;
PTLC is preparative thin layer chromatography;
EtSNa is sodium ethanethiolate;
Calcd is calculated;
AIBN is 2,2'-azobisisobutyronitrile;
Sat'd is saturated;
NaOEt is sodium ethoxide;
h is hour; and
min is minutes.

General Methods of Preparation

Compounds of Formulae Ia and Ib can be prepared by any method known to those skilled in the art, preferably according to the following general Schemes 1–4.

Examples 1, 1.3.2, 2, 3, 7, 8, and 12–24 were prepared according to Scheme 1.

27
-continued
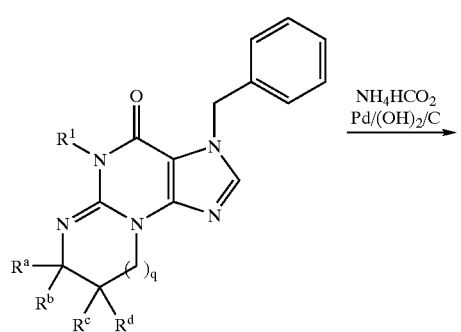
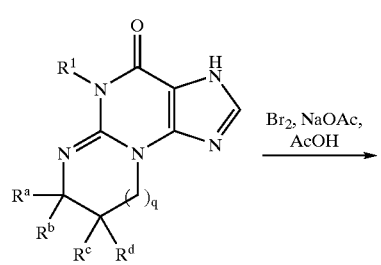
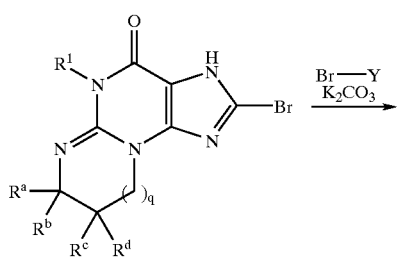
28
-continued
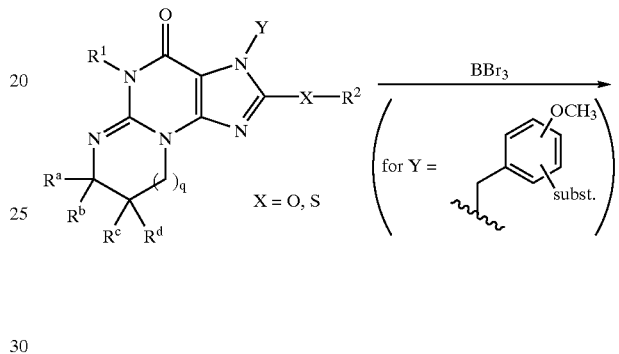
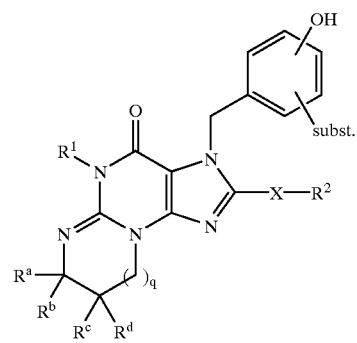
Examples 4–6 and 9–10 were prepared according to the general Scheme 2.
Scheme 2
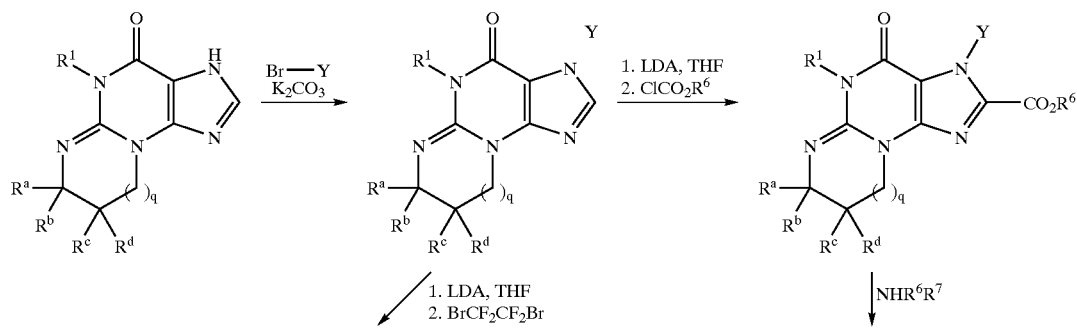

-continued
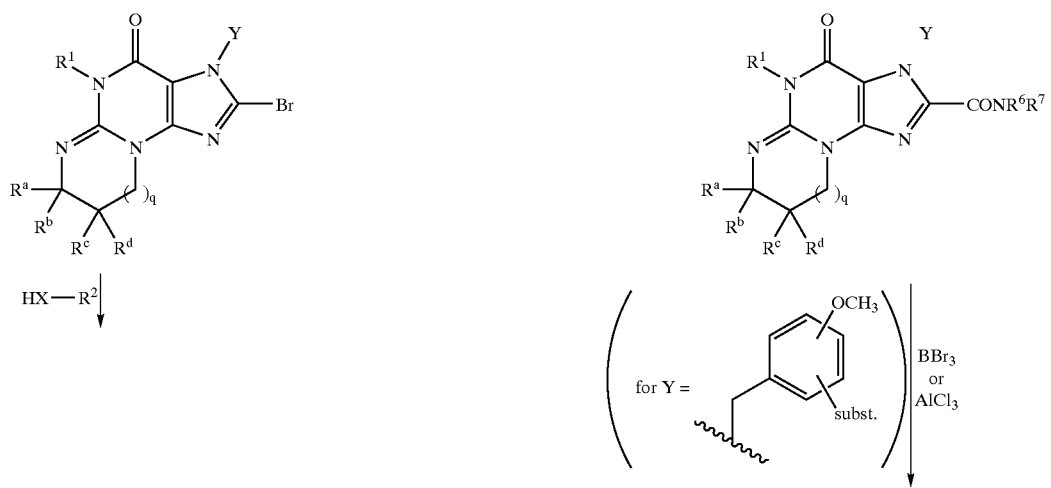
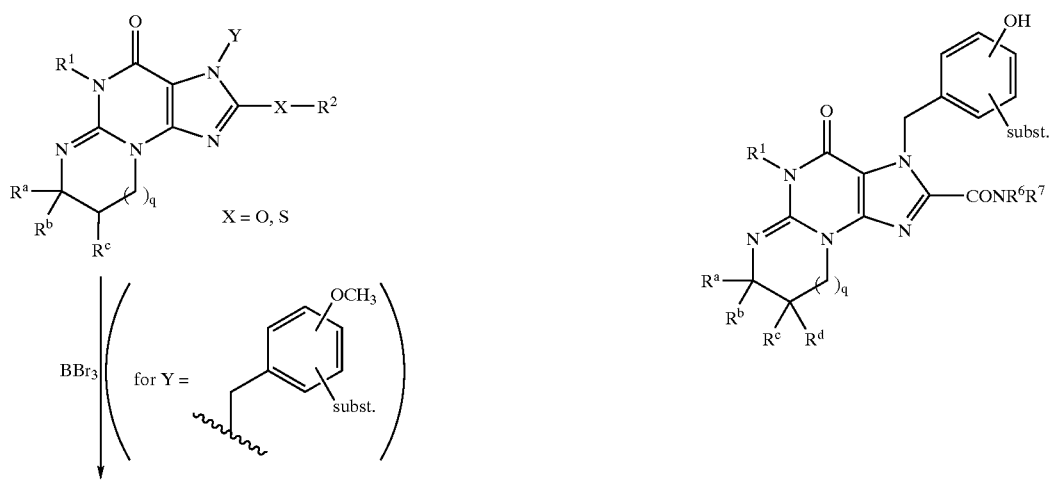
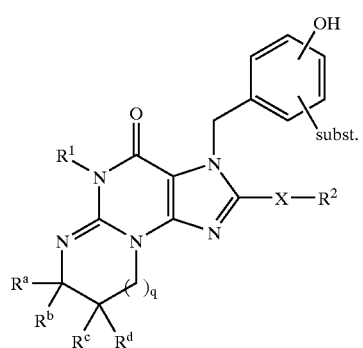

Example 11 was prepared according to the general Scheme 3:
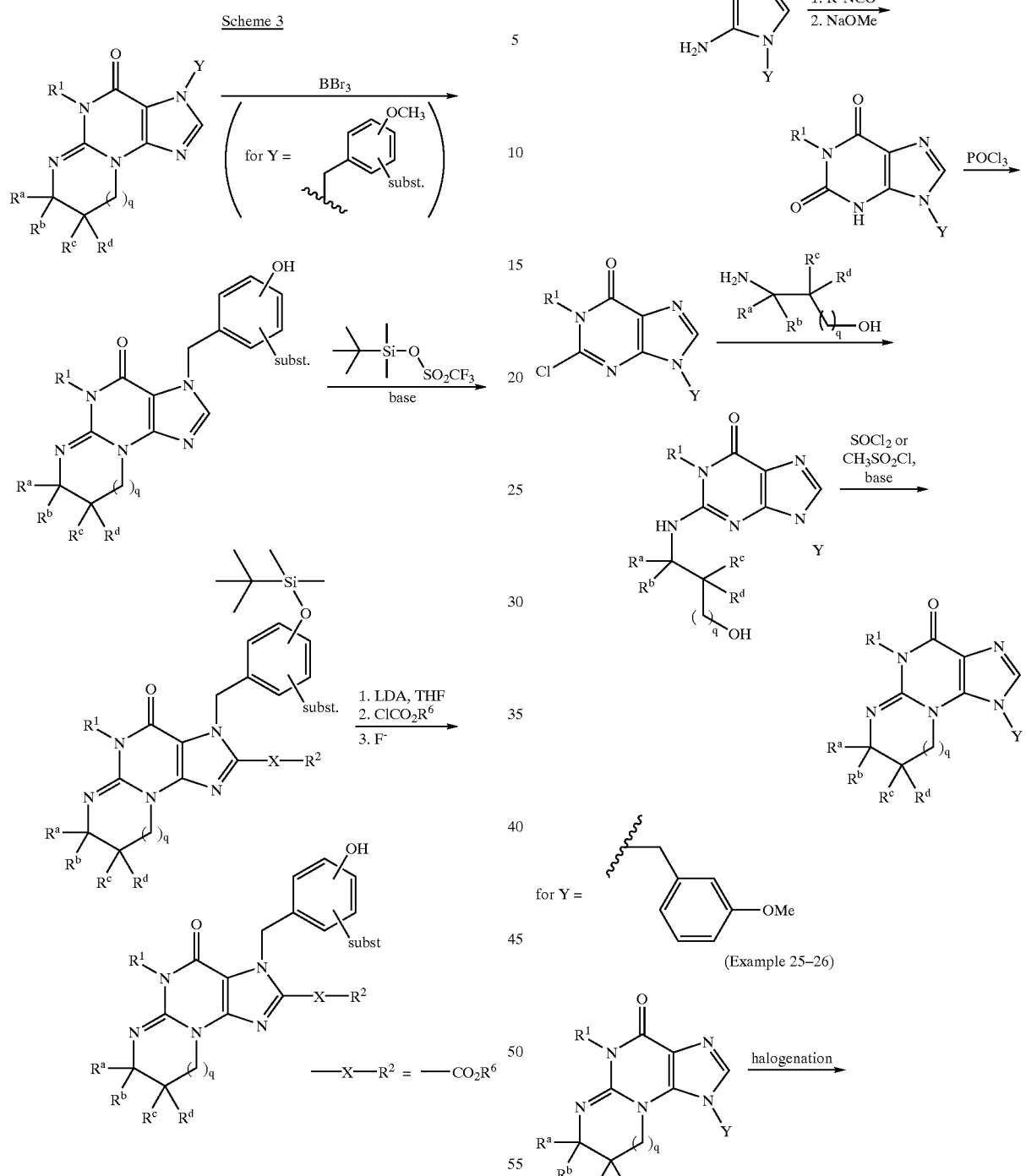
Examples 25–27 were prepared according to the general Scheme 4.
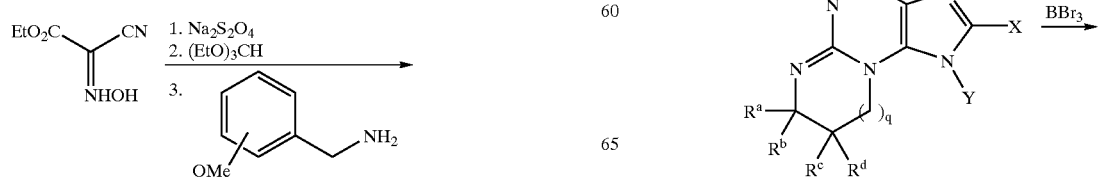

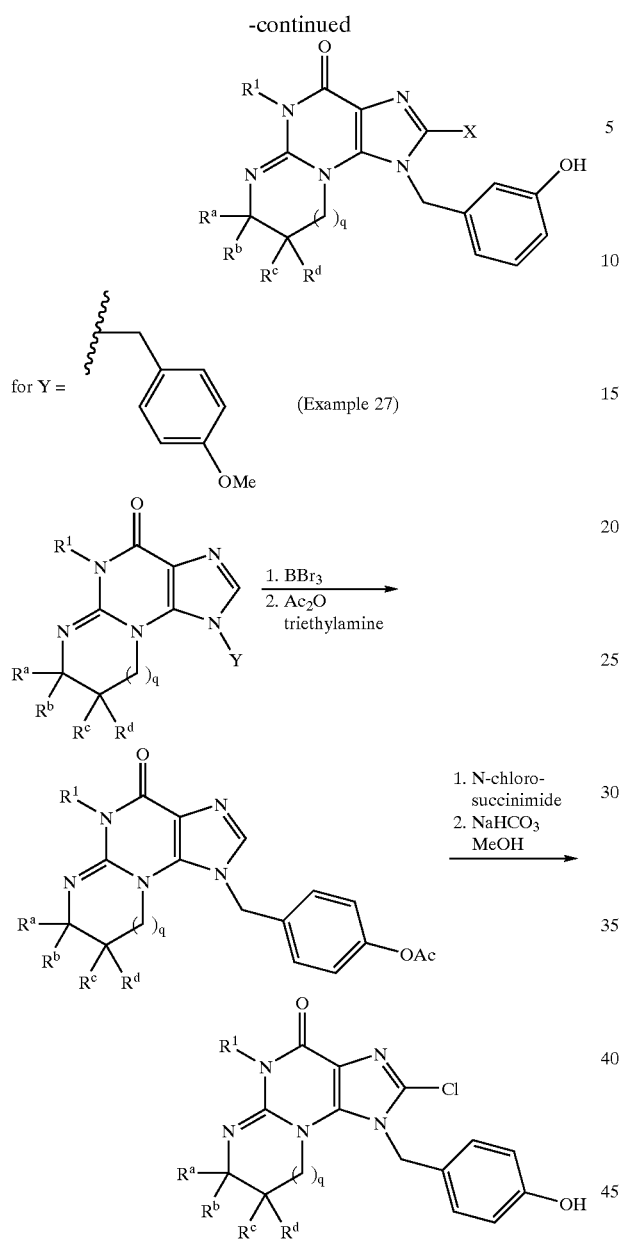

(Example 27)

Process for Preparation of Intermediate I

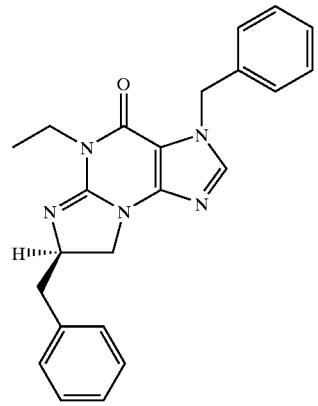

I

Step 1

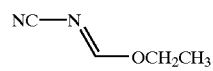

A mixture of cyanamide (320 g, 7.62 mol) and triethyl orthoformate (2.2 L) was refluxed under $N_2$ for 3 h. The reaction mixture was allowed to cool, and ethanol was removed by distillation. Fractional distillation of the residue (0.5 mm Hg, 50–60° C.) afforded the product (656 g, 88%). $^1$H NMR (300 MHz, CDCl$_3$) δ 8.40 (1H, s), 4.39 (2H, q, J=7 Hz), 1.39 (3H, t, J=7 Hz).

Step 2

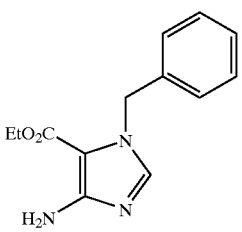

PREPARATION OF EXAMPLE COMPOUNDS

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min—10% CH$_3$CN, 5 min—95% CH$_3$CN, 7 min—95% CH$_3$CN, 7.5 min—10% CH$_3$CN, 9 min—stop. The retention time and observed parent ion are given.

To a solution of the product of Step 1 (704 g, 7.2 mol) in Et$_2$O (600 ml) was added N-benzylglycine ethyl ester (1,300 g, 6.73 mol) over 0.5 h. The reaction mixture was stirred for 2 h, then concentrated. EtOH (500 ml) was added, and the mixture was evaporated to dryness. The residue was dissolved in EtOH (2.5 L), cooled in an ice bath, and 20% sodium ethoxide in EtOH (2.3 L) was added over 40 min. After the addition was completed, the reaction mixture was stirred at room temperature for 1 h, then stored overnight in a refrigerator. The solid was collected, washed with cold EtOH, and dried at 55° C. in vacuo to give the product (1,219 g, 70%). $^1$H NMR (300 MHz, CDCl$_3$) δ 7.38–7.20 (4H, m), 7.17–7.12 (2H, m), 5.38 (2H, s), 4.8 (2H, b), 4.23 (2H, q, J=7 Hz), 1.23 (3H, t, J=7 Hz).

Step 3

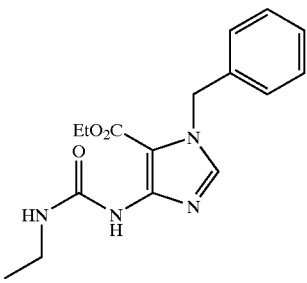

A mixture of the product of Step 2 (1,219 g, 4.97 mol), o-xylene (7.5 L), and ethyl isocyanate (425 g, 5.98 mol) was refluxed for 16 h. The reaction mixture was allowed to cool and the solvent was removed by distillation. The residue was triturated with Et$_2$O (1 L), and the solid was collected and dried in vacuo (50° C.) to give the product (1,310 g, 84%). $^1$H NMR (300 MHz, CDCl$_3$) δ 8.60 (1H, b), 7.90 (1H, b), 7.40–7.23 (4H, m), 7.16 (2H, m), 5.41 (2H, s), 4.23 (2H, q, J=7 Hz), 3.39 (2H, q, J=7 Hz), 1.30 (3H, t, J=7 Hz), 1.25 (3H, t, J=7 Hz).

Step 4

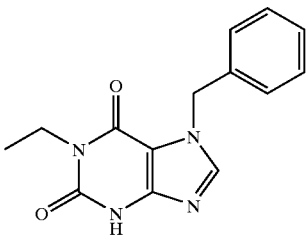

To a suspension of the product of Step 3 (1,310 g, 4.15 mol) in MeOH (5 L) was added sodium methoxide (500 g, 9.25 mol) in portions. The reaction mixture was refluxed for 4 h, then approximately 4 L of MeOH was distilled from the reaction mixture. The residue was poured into ice-water (5 L) and conc. HCl (1.8 L) was added. The white precipitate was collected, washed with water, and dried in vacuo (60° C.) to give the product (1,053 g, 94%). $^1$H NMR (DMSO-d6) δ 8.18 (1H, s), 7.38–7.25 (5H, m), 5.43 (2H, s), 3.81 (2H, q, J=7 Hz), 1.05 (3H, t, J=7 Hz).

Step 5

A

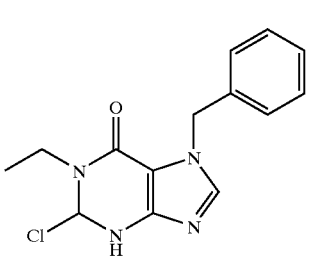

A suspension of the product of Step 4 (523 g, 1.93 mol) in POCl$_3$ (6 L) was refluxed under N$_2$ for 16 h, then approximately 4.5 L POCl$_3$ was distilled from the reaction mixture. The residue was poured onto ice and 50% NaOH was slowly added, along with the addition of ice to maintain the temperature at 0° C., until pH 6–7. The whole was extracted with CH$_2$Cl$_2$ (24 L) and the organic layer was dried (MgSO$_4$), filtered and concentrated. The residue was subjected to flash chromatography (EtOAc) to give the product A (351.1 g, 63%). $^1$H NMR (300 MHz, CDCl$_3$) δ 7.82 (1H, s), 7.40–7.30 (5H, m), 5.28 (2H, s), 4.37 (2H, q, J=7 Hz), 1.39 (3H, t, J=7 Hz).

Step 6

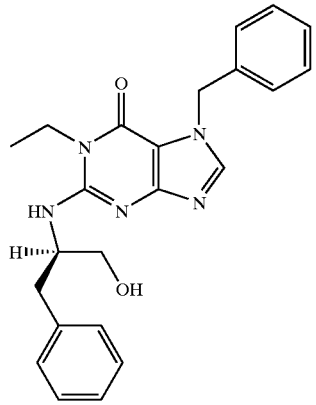

A mixture of the product A (75 g, 0.26 mol), (R)-2-amino-3-phenyl-1-propanol (59 g, 0.39 mol), iPr$_2$NEt (186 ml, 1.1 mol) and 1-methyl-2-pyrrolidinone (370 ml) was heated at 130° C. for 12 h. The reaction mixture was allowed to cool, then poured into 8 L of water and extracted with CH$_2$Cl$_2$ (2×8 L). The combined organic layers were concentrated, and the residue was subjected to vacuum distillation (18 mm Hg) to remove 1-methyl-2-pyrrolidinone. The residue was triturated with ice-water to afford a semi-solid that was dissolved in MeOH, and the resultant solution was evaporated to dryness to give the product as a foam (94.5 g, 90%). $^1$H NMR (300 MHz, CDCl$_3$) δ 7.63 (1H, s), 7.40–7.20 (10H, m), 5.45 (2H, s), 4.65 (1H, m), 4.45 (1H, m), 3.96 (1H, m), 3.91 (1H, m), 3.80 (1H, m), 3.76 (1H, m), 3.09 (1H, m), 2.95 (1H, m), 1.02 (3H, t, J=7 Hz).

Step 7

To an ice-cold solution of the product of Step 6 (94.5 g, 0.24 mol) and Et$_3$N (100 ml, 0.72 mol) in CH$_2$Cl$_2$ (1 L) was added methanesulfonyl chloride (41.2 g, 0.36 mol) dropwise over 0.5 h. After 0.5 h, the reaction mixture was refluxed for 2 h, then diluted with CH$_2$Cl$_2$ (2 L) and washed with sat'd NaHCO$_3$. The organic layer was dried (MgSO$_4$), filtered and evaporated. The residue was subjected to flash chromatography (EtOAc) to give Intermediate I (58 g, 63%). $^1$H NMR (300 MHz, CDCl$_3$) δ 7.40–7.20 (11H, m), 5.41 (2H, s), 4.50 (1H, m), 4.09 (2H, m), 3.95 (1H, m), 3.95 (1H, m), 3.81 (1H, m), 3.22 (1H, m), 2.72 (1H, m), 1.30 (3H, t, J=7 Hz).

Process for Preparation of Intermediate II

II

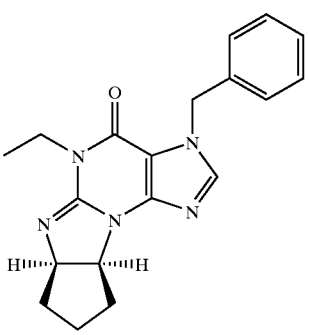

Reaction of A with (1R, 2R)-2-aminocyclopentanol according to essentially the same procedure as outlined in Intermediate 1, Step 6, and subjection of the product to methanesulfonyl chloride by essentially the same procedure described for Intermediate I, Step 7 afforded Intermediate II. HRMS Calcd for $C_{19}H_{21}N_5O$: 336.1824, Found: 336.1833.

Process for Preparation of Intermediate III

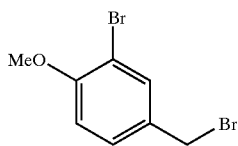
III

To a solution of 3-bromo-4-methoxytoluene (11 g, 54.7 mmol) in $CH_2Cl_2$ (100 ml) under $N_2$, was added N-bromosuccinimide (10.7 g, 60.2 mmol) and AIBN (82 mg, 0.5 mmol). The resulting mixture was refluxed overnight, then cooled in an ice-water bath. The solid that precipitated was removed by filtration. The filtrate was washed with water (×2), brine (×1), dried ($Na_2SO_4$), filtered and concentrated. After drying under vacuum, Intermediate III (16.4 g, 100%) was obtained as a white solid that was used without further purification. $^1H$ NMR (300 MHz, $CDCl_3$) δ 7.58 (1H, d, J=2.1 Hz), 7.29 (1H, dd, J=8.1, 2.1 Hz), 6.84 (1H, d, J=8.1 Hz), 4.43 (2H, s), 3.88 (3H, s).

Process for Preparation of Intermediate IV

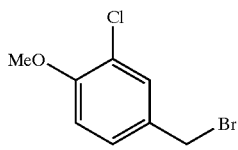
IV

Reaction of 3-chloro-4-methoxytoluene, N-bromosuccinimide and AIBN by essentially the same procedure described for Intermediate III gave Intermediate IV. $^1H$ NMR (300 MHz, $CDCl_3$) δ 7.42 (1H, d, J=2.4 Hz), 7.26 (1H, dd, J=8.4, 2.4 Hz), 6.84 (1H, d, J=8.4 Hz), 4.44 (2H, s), 3.91 (2H, s).

EXAMPLE 1

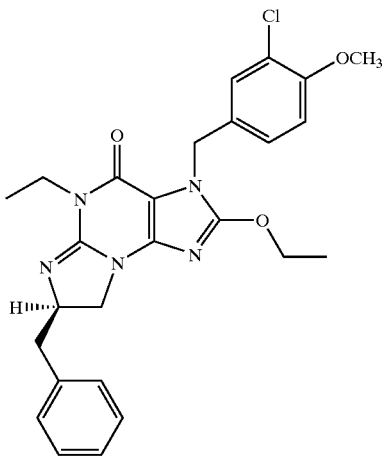
1

Step 1

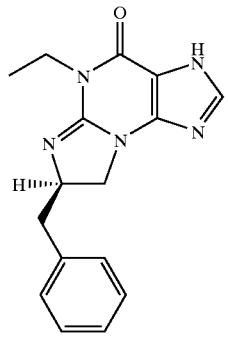
1.1.1

A mixture of Intermediate I (58 g, 0.15 mol), ammonium formate (350 g, 5.5 mol) and 20% $Pd(OH)_2/C$ (25 g) in MeOH (1.3 L) was refluxed for 3 h. The reaction mixture was allowed to cool, additional ammonium formate (100 g, 1.6 mol) and 20% $Pd(OH)_2/C$ (25 g) was added, and the mixture was refluxed for 2 h. The reaction mixture was filtered and the filtrate was concentrated. The residue was dissolved in $CH_2Cl_2$ (3 L), washed with sat'd $NaHCO_3$, dried ($MgSO_4$), filtered and evaporated to give the product (37 g, 84%). $^1H$ NMR (300 MHz, $CDCl_3$) δ 7.62 (1H, s), 7.35–7.18 (5H, m), 4.55 (1H, m), 4.19–3.95 (3H, m), 3.90 (1H, m), 3.21 (1H, m), 2.78 (1H, m), 1.35 (3H, t, J=7 Hz).

Step 2

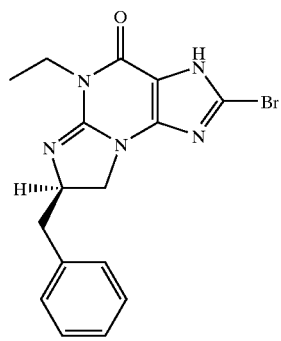
1.2.1

To a solution of the product of Step 1 (17 g, 58 mmol) in AcOH (700 ml) was added sodium acetate (10 g, 0.12 mol) and $Br_2$ (12.5 g, 78 mmol), and the reaction mixture was stirred at 50° C. for 12 h. After the reaction mixture had cooled to room temperature, sodium bisulfite (40 g) was added and the whole was concentrated. The residue was taken up in $CH_2Cl_2$, washed with sat'd $NaHCO_3$, dried ($MgSO_4$), filtered and evaporated to give the product (17 g, 80%). $^1H$ NMR (300 MHz, $CDCl_3$) δ 7.32–7.15 (5H, m), 4.88 (1H, m), 4.37 (1H, m), 4.17 (3H, m), 3.26 (1H, m), 3.02 (1H, m), 1.25 (3H, t, J=7 Hz).

Step 3

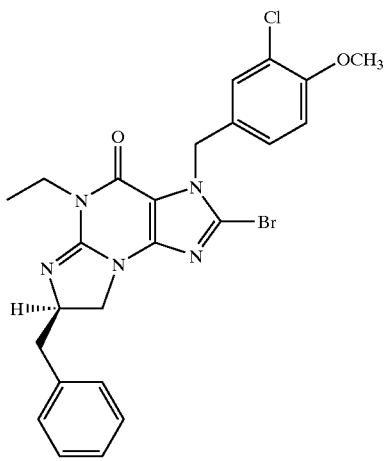

1.3.1

To a suspension of the product of Step 2 (500 mg, 1.34 mmol) and K$_2$CO$_3$ (0.55 g, 4.0 mmol) in DMF (6 ml) was added 3-chloro-4-methoxybenzyl bromide (Intermediate IV) (0.94 g, 4.0 mmol) and the reaction mixture was stirred overnight. Water (30 ml) was added and the whole was extracted with EtOAc (3×20 ml). The combined organic layers were washed with water, dried (over MgSO$_4$), filtered and evaporated. The residue was subjected to PTLC (3:97 MeOH/CH$_2$Cl$_2$) to give the product (0.38 g, 54%) $^1$H NMR (300 MHz, CDCl$_3$) δ 7.40–7.19 (7H, m), 6.86 (1H, d, J=11.6 Hz), 5.37 (2H, s), 4.44 (1H, m), 4.00 (2H, m), 3.88–3.75 (2H, m), 3.86 (3H, s), 3.18 (1H, dd, J=18.0, 6.0 Hz), 2.69 (1H, dd, J=18.0, 12.4 Hz), 1.29 (3H, t, J=9.2 Hz).

The following compounds were prepared similarly to the above procedures:

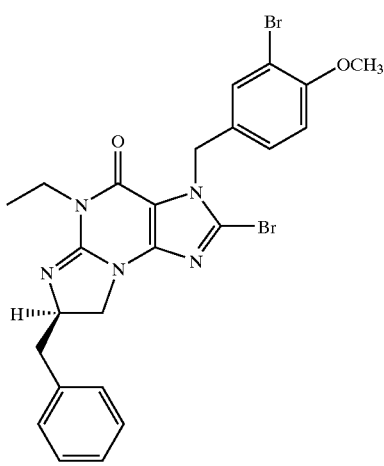

1.3.2

MS (ES) m/e 572 (M+H)$^+$.

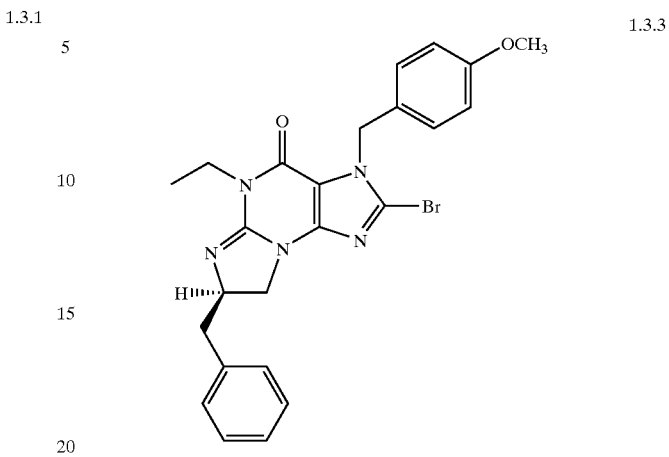

1.3.3

MS (ES) m/e 494 (M+H)$^+$.

Step 4

To a solution of the product 1.3.1 of Example 1, Step 3 (1.6 g, 3.1 mmol) in DMF (47 ml) was added a solution of NaOEt in ethanol (21% ethanol solution). The reaction mixture was allowed to stir at room temperature for 16 h. The reaction mixture was diluted with CH$_2$Cl$_2$ (150 ml) and the organic layer was washed with water (3×25 ml). The organic layer was dried with Na$_2$SO$_4$, filtered and concentrated to give a viscous oil. The crude product was purified by SiO$_2$ chromatography (95:5 CH$_2$Cl/MeOH) to afford the Product 1 (1.48 g, 98%). $^1$H NMR (300 MHz, CDCl$_3$) δ 7.42–7.18 (7H, m), 6.92–6.83 (1H, m), 5.22 (2H, s), 4.64–4.42 (3H, m), 4.22–3.75 (5H, m), 3.88 (3H, s), 3.38–3.23 (1H, m), 2.85–2.64 (1H, m), 1.48–1.38 (3H, m), 1.36–1.23 (3H, m). MS (ES) m/e 494 (M+H)$^+$.

EXAMPLE 2

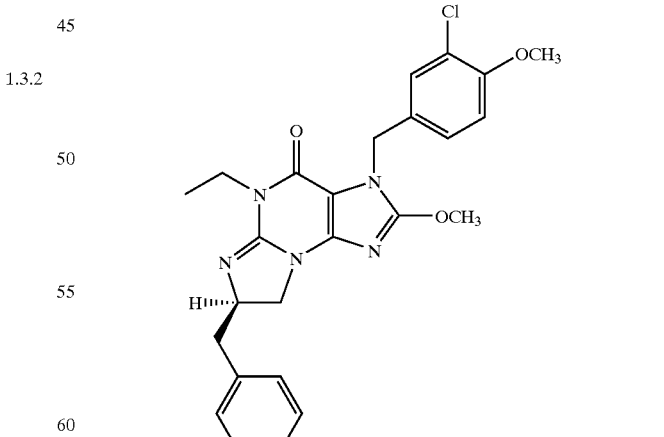

2

The product of Example 1, Step 3 (1.3.1) was treated with sodium methoxide in methanol by essentially the procedure described in Example 1, Step 4, to give the Product 2 shown above. ¹H NMR (300 MHz, CDCl₃) δ 7.34 (1H, s), 7.28–7.13 (6H, m), 6.81 (1H, d, J=8.0 Hz), 5.06 (2H, s), 4.41 (1H, m), 4.04 (3H, s), 4.02–3.92 (2H, m), 3.86–3.81 (2H, m), 3.81 (3H, s), 3.68 (1H, dd, J=6.5, 10.2 Hz), 3.18 (1H, dd, J=4.4, 13.2 Hz), 2.63 (1H, dd, J=9.5, 13.2 Hz), 1.25 (3H, t, J=6.6 Hz). MS (ES) m/e 480 (M+H)⁺.

EXAMPLE 3

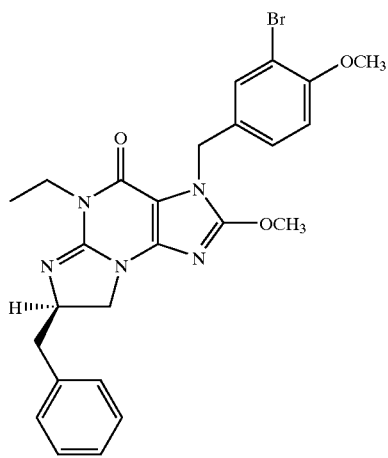

3

The product of Example 1, Step 3 (1.3.2) was treated with sodium methoxide in methanol by essentially the procedure described in Example 1, Step 4, to give the Product 3 shown above. ¹H NMR (300 MHz, CDCl₃) δ 7.51 (1H, d, J=2.2 Hz), 7.31 (1H, dd, J=2.2, 8.2 Hz), 7.28–7.14 (5H, m), 6.79 (1H, d, J=8.2 Hz), 5.07 (2H, s), 4.45 (1H, m), 4.04 (3H, s), 4.00 (2H, m), 3.86 (1H, t, J=9.9 Hz), 3.81 (3H, s), 3.71 (1H, dd, J=6.6, 9.9 Hz), 3.20 (1H, dd, J=4.4, 13.2 Hz), 2.67 (1H, dd, J=9.3, 13.2 Hz), 1.26 (3H, t, J=7.2 Hz). MS (ES) m/e 524 (M+H)⁺.

EXAMPLE 4

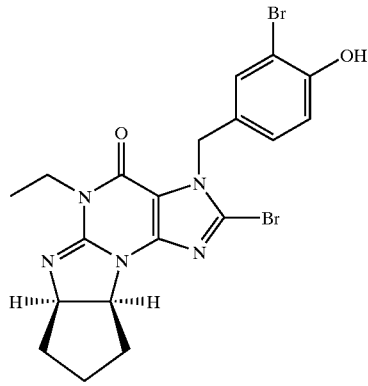

4

Step 1

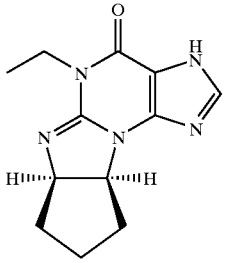

4.1.1

Reaction of Intermediate II with Pd(OH)₂/C and ammonium formate in MeOH by essentially the procedure described in Example 1, Step 1 gave the Product 4.1.1 shown above. ¹H NMR (300 MHz, CDCl₃) δ 7.81 (s, 1H), 6.1 (br,1H), 5.03 (1H, t, J=7.2 Hz), 4.86 (1H, t, J=7.2 Hz), 4.05 (2H, m), 2.35 (1H, m), 2.15 (1H, m), 2.00–1.80 (3H, m), 1.62 (1H, m), 1.24 (3H, t, J=7.2 Hz). MS (ES) m/e 246 (M+H)⁺.

Step 2

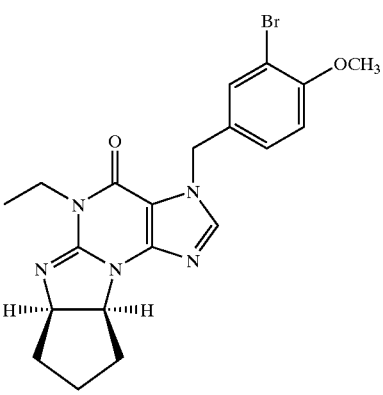

4.2.1

A mixture of the product of Step 1 (4.1.1) (2.10 g, 8.5 mmol), 3-bromo-4-methoxybenzyl bromide (Intermediate III) (3.60 g, 12.87 mmol), and K₂CO₃ (3.55 g, 25.7 mmol) was stirred overnight, diluted with dichloromethane, washed with water, dried (Na₂SO₄), filtered, and concentrated. The residue was purified by flash chromatography to yield the Product 4.2.1 (gradient 99:1–97:3 CH₂Cl₂/MeOH) to give the product (3.02 g, 79%). MS (ES) m/e 444 (M+H)⁺.

Reaction of the product of Step 1 (4.1.1) with 3-chloro-4-methoxybenzyl bromide (Intermediate IV) by essentially the same procedure afforded the following product:

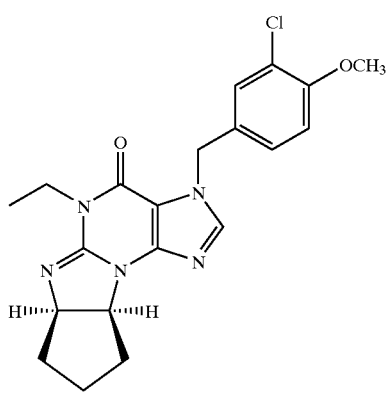

4.2.2

MS (ES) m/e 400 (M+H)⁺.

Step 3

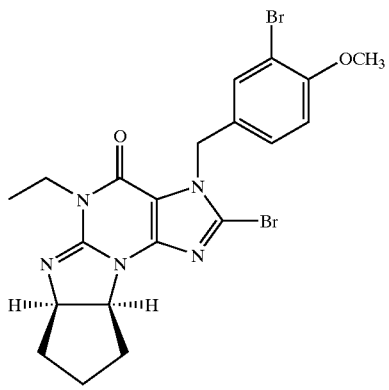

4.3.1

To a solution of the product of Step 2 (4.2.1) (300 mg, 0.675 mmol) in THF at −78° C. was added dropwise a 2M solution of LDA in THF (0.51 ml). The mixture was stirred in the cold for 25 min followed by the addition of 1,2-dibromotetrafluoroethane (349 mg, 1.35 mmol). The mixture was stirred for 1 h at −78° C., quenched with sat'd NaHCO$_3$, extracted with CH$_2$Cl$_2$, dried (over Na$_2$SO$_4$), filtered and concentrated. Subjection of the residue to PTLC gave the Product 4.3.1 (266 mg, 75%). MS (ES) m/e 522 (M+H)$^+$.

Use of the appropriate starting material and essentially the same procedure disclosed above afforded the following product.

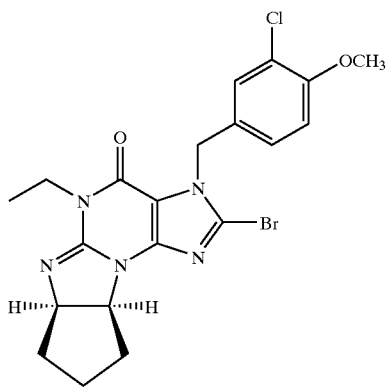

4.3.2

MS (ES) m/e 478 (M+H)$^+$.

Step 4

To a mixture of the product of Example 4, Step 3 (4.3.1) (20 mg, 0.038 mmol) and CH$_2$Cl$_2$ (1 ml) was added 1M solution of BBr$_3$ in CH$_2$Cl$_2$ (0.2 ml, 0.19 mmol). The mixture was stirred for 30 min, quenched with aq. NH$_3$, extracted with CH$_2$Cl$_2$, dried (over Na$_2$SO$_4$), filtered and evaporated to afford the Product 4 shown above (15 mg, 76%). $^1$H NMR (300 MHz, CDCl$_3$) δ 7.58 (1H, d, J=1.7 Hz), 7.31 (1H, dd, J=1.7, 8.2 Hz), 6.97 (1H, d, J=8.2 Hz), 5.34 (2H, s), 4.79 (1H, t, J=7.0 Hz), 4.71 (1H, t, J=7.0 Hz), 4.0 (2H, q, J=7.0 Hz), 2.21 (1H, dd, J=6.0, 13 Hz), 1.95 (1H, m), 1.78 (3H, m), 1.54 (1H, m), 1.25 (3H, t, J=7.0 Hz). MS (ES) m/e 508 (M+H)$^+$.

EXAMPLE 5

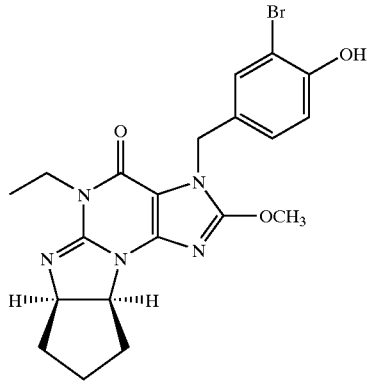

5

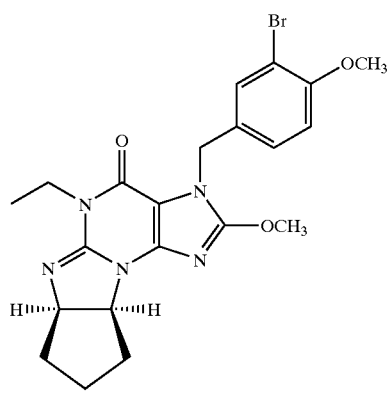

5.1.1

To a mixture of sodium methoxide (193 mg, 72 mmol) in MeOH (5 ml) was added the product of Example 4, Step 3 (4.3.1) (60 mg, 0.11 mmol). The mixture was briefly brought to reflux until a solution was obtained, then stirred for 8 h at room temperature, poured into water, extracted with CH$_2$Cl$_2$, dried (Na$_2$SO$_4$), filtered, and the volatiles were evaporated to give the Product 5.1.1 (46 mg, 85%). MS (ES) m/e 474 (M+H)$^+$.

Step 2

The product of Step 1 (5.1.1) was demethylated according to the procedure of Example 4, Step 4 to give the Product 5 above. $^1$H NMR (300 MHz, CDCl$_3$) δ 7.51 (1H, s), 7.25 (1H, m), 6.89 (1H, d, J=7.7 Hz), 5.08 (2H, s), 4.69 (2H, m), 4.12 (3H, s), 3.95 (2H, m), 3.58 (1H, br), 2.18 (1H, m), 2.0–1.40 (5H, m), 1.22 (3H, t, J=6.9 Hz). MS (ES) m/e 460 (M+H)$^+$.

EXAMPLE 6

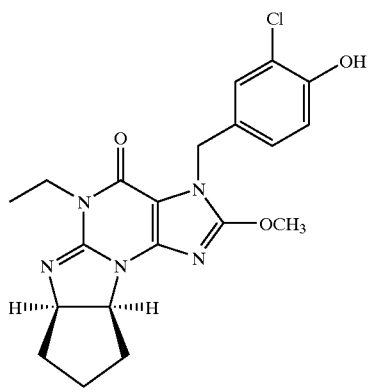

6

Step 1

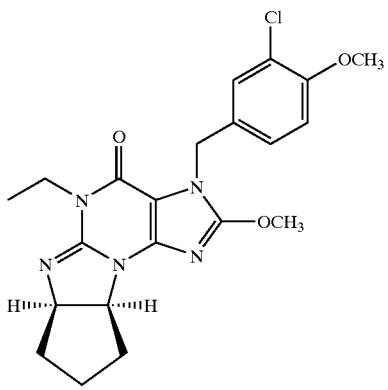

6.1.1

The product of Example 4, Step 3 (4.3.2) was treated with sodium methoxide as described in Example 5, Step 1 to yield Product 6.1.1. MS (ES) m/e 430 (M+H)$^+$.

Step 2

The product of Step 1 (6.1.1) was demethylated according to the procedure of Example 4, Step 4 to give the Product 6. $^1$H NMR (300 MHz, CDCl$_3$) δ 7.37 (1H, m), 7.21 (1H, m), 6.90 (1H, m), 5.08 (2H, s), 4.69 (2H, m), 4.12 (3H, s), 3.95 (2H, m), 2.18 (1H, m), 2.0–1.40 (5H, m), 1.22 (3H, t, J=6.3 Hz). MS (ES) m/e 416 (M+H)$^+$.

EXAMPLE 7

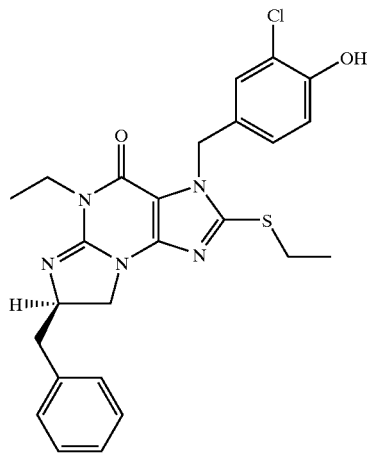

7

Step 1

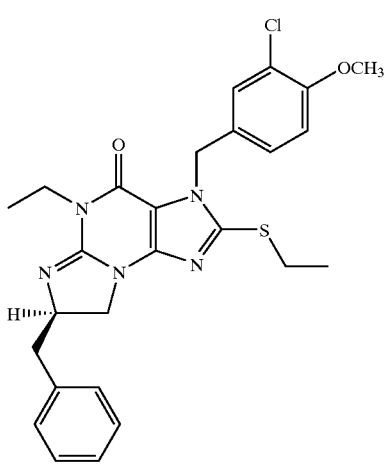

7.1.1

To a solution of the product of Example 1, Step 3 (1.3.1) (220 mg, 0.42 mmol) in 5.0 ml of DMF was added EtSNa (350 mg, 4.17 mmol). The reaction mixture was stirred at room temperature for 16 h. The reaction mixture was diluted with CH$_2$Cl$_2$ (50 ml) and the organic layer was washed with water (3×20 ml). The organic layer was dried (Na$_2$SO$_4$), filtered and concentrated. The crude product was purified by SiO$_2$ chromatography (95:5 CH$_2$Cl$_2$/MeOH) to give the product 7.1.1 (80 mg, 38%). $^1$H NMR (300 MHz, CDCl$_3$) δ 7.46–7.18 (m, 7H), 6.92–6.83 (m, 1H), 5.39–5.28 (m, 2H), 4.59–4.46 (m, 1H), 4.19–3.73 (m, 4H), 3.87 (s, 3H), 3.34–3.12 (m, 3H), 2.80–2.64 (m, 1H), 1.41–1.22 (m, 6H). MS (ES) m/e 510 (M+H)$^+$.

Step 2

Reaction of the product of Step 1 (7.1.1) with BBr$_3$ by essentially the procedure of Example 4, Step 4 gave the Product 7. $^1$H NMR (300 MHz, CDCl$_3$) δ 7.41–7.18 (7H, m), 7.05–6.95 (1H, m), 5.31 (2H, s), 4.65–4.48 (1H, m), 4.23–3.68 (4H, m), 3.38–3.15 (4H, m), 2.90–2.70 (1H, m), 1.42–4.27 (3H, m), 1.19 (3H, m). MS (ES) m/e 496 (M+H)$^+$.

EXAMPLE 8

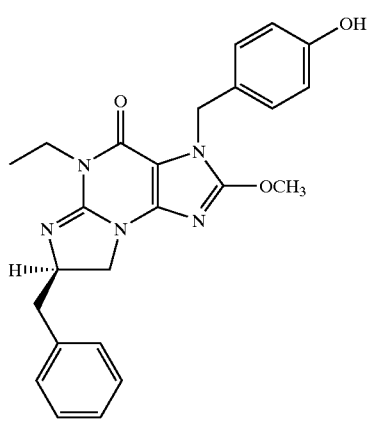

8

Step 1

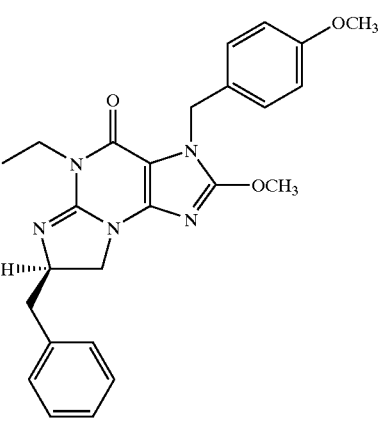

8.1.1

The product of Example 1, Step 3 (1.3.3) was treated with sodium methoxide in methanol using conditions of Example 1, Step 4 to give the product 8.1.1. $^1$H NMR (300 MHz, CDCl$_3$) δ 7.34–7.17 (7H, m), 6.81 (2H, d, J=8.2 Hz), 5.11 (2H, s), 4.44 (1H, m), 4.05 (3H, s), 4.06–3.94 (2H, m), 3.85 (1H, t, J=9.5 Hz), 3.74 (3H, s), 3.72–3.67 (1H, m), 3.20 (1H, dd, J=4.4, 13.5 Hz), 2.65 (1H, dd, J=9.4, 13.5 Hz), 1.28 (3H, t, J=6.9 Hz). MS (ES) m/e 446 (M+H)$^+$.

Step 2

Reaction of the product of step 1 (8.1.1) with BBr$_3$ by essentially the procedure of Example 4, Step 4 gave the Product 8. $^1$H NMR (300 MHz, CDCl$_3$) δ 7.28–7.16 (7H, m), 6.76 (2H, d, J=8.2 Hz), 5.11 (2H, s), 4.48 (1H, m), 4.08 (3H, s), 4.00 (2H, m), 3.90 (1H, t, J=9.9 Hz), 3.75 (1H, dd, J=6.5, 9.9 Hz), 3.22 (1H, dd, J=4.4, 9.4 Hz), 2.67 (1H, dd, J=9.3, 13.7 Hz), 1.26 (3H, t, J=7.1Hz). MS (ES) m/e 432 (M+H)$^+$.

EXAMPLE 9

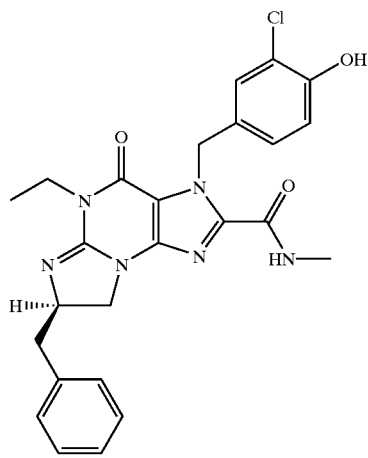

9

Step 1

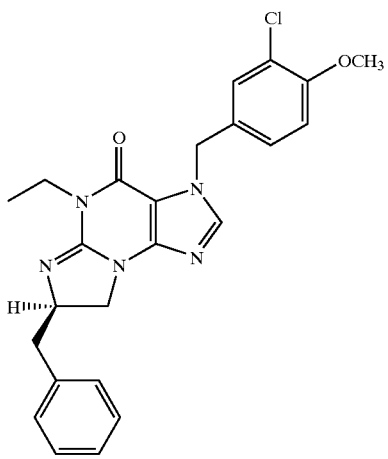

9.1.1

The product of Example 1, Step 1 was alkylated with 3-chloro-4-methoxybenzylbromide (Intermediate IV) using conditions of Example 1, Step 3 to give the product 9.1.1. MS (ES) m/e 450 (M+H)$^+$.

Step 2

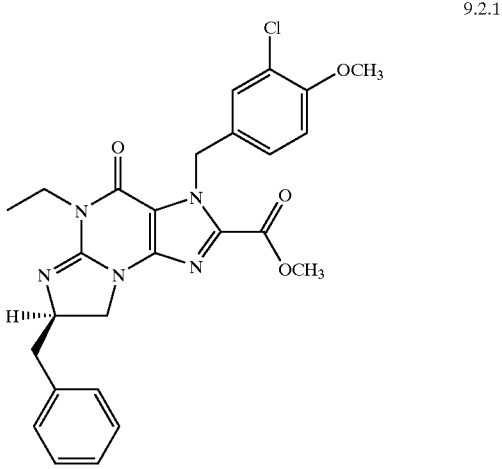

9.2.1

To a solution of the product of Step 1 (9.1.1) (2.71 g, 6.03 mmol) in THF (20 ml) at −78° C. was added 2M LDA in THF (5.4 ml, 10.9 mmol). The mixture was stirred for 25 min, then methyl chloroformate (2.27 g, 24.1 mmol) was added. The mixture was stirred in the cold for 25 min, quenched with sat'd NH$_4$Cl, cooling was removed and the product was extracted with CH$_2$Cl$_2$. The organic layer was dried (Na$_2$SO$_4$), filtered and evaporated. Subjection of the residue to flash chromatography (gradient from 1:1 to 7:3 EtOAc/hexanes) gave the product 9.2.1 (1.40 g, 45%). MS (ES) m/e 508 (M+H)$^+$.

Step 3

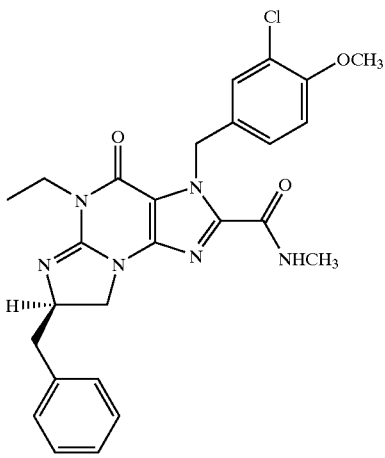

9.3.1

A mixture of the product of Step 2 (9.2.1) (40 mg) and 2M solution of methylamine in THF (4.0 ml) was heated in a sealed tube at 80° C. for 48 h. The solvent was evaporated and the product was purified by PTLC (5:95 MeOH/CH$_2$Cl$_2$) to give the product 9.3.1 (41 mg). MS (ES) m/e 507 (M+H)$^+$.

Step 4

The product of Step 3 (9.3.1) was demethylated using conditions of Example 4, Step 4 to yield the Product 9. $^1$H NMR (300 MHz, CDCl$_3$) δ 7.51 (1H, s), 7.38–7.17 (6H, m), 6.93 (1H, d, J=8.2 Hz), 5.99 (2H, s), 5.30 (1H, br), 4.51 (1H, br), 4.06 (2H, m), 3.88 (1H, t, J=9.3 Hz), 3.73 (1H, m), 3.24 (1H, dd, J=4.9, 13.7 Hz), 2.98 (3H, d, J=4.9 Hz), 2.69 (1H, dd, J=9.3, 13.7 Hz), 1.78 (1H, br), 1.31 (3H, t, J=7.1 Hz). MS (ES) m/e 493 (M+H)$^+$.

EXAMPLE 10

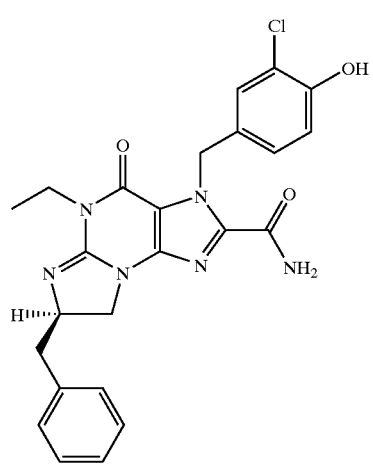

10

Step 1

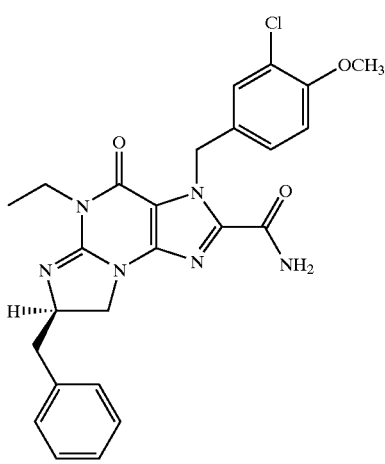

10.1.1

A mixture of 40 mg of the product of Example 9, Step 2 (9.2.1) was dissolved in 7N NH$_3$ in MeOH (3.0 ml) and stirred for 48 h. The volatiles were evaporated and the residue purified by PTLC to give the product 10.1.1 (35 mg). MS (ES) m/e 493 (M+H)$^+$.

Step 2

To a mixture of the product of Step 1 (10.1.1) (500 mg, 1.01 mmol), ethanethiol (5.0 ml) and CH$_2$Cl$_2$ (5.0 ml) at 0° C. was added in one lot aluminum chloride (811 mg, 6.08 mmol). The mixture was vigorously stirred for 20 min and quenched with of sat'd NaHCO$_3$ (20 ml). The mixture was transferred into a separatory funnel using small portions of MeOH to dissolve otherwise insoluble material deposited on the walls of the flask. Sodium potassium tartrate was added, and the mixture was extracted with CH$_2$Cl$_2$. The organic phase was dried (over Na$_2$SO$_4$), filtered and concentrated, and the residue was subjected to flash chromatography (3:97 to 5:95 MeOH/CH$_2$Cl$_2$) to give the Product 10 (456 mg, 93%). $^1$H NMR (300 MHz, CDCl$_3$) δ 7.51 (1H, s), 7.38–7.17 (6H, m), 6.92 (1H, d, J=8.2 Hz), 5.97 (2H, s), 5.57 (1H, br), 4.51 (1H, br), 4.,07 (2H, m), 3.90 (1H, t, J=9.8 Hz), 3.74 (1H, m), 3.24 (1H, dd, J=3.8, 13.7 Hz), 2.70 (1H, dd, J=9.3, 13.7 Hz), 1.93 (2H, br), 1.31 (3H, t, J=7.1Hz). MS (ES) m/e 479 (M+H)$^+$.

EXAMPLE 11

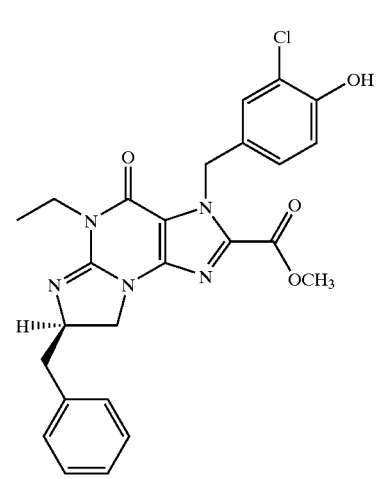

11

Step 1

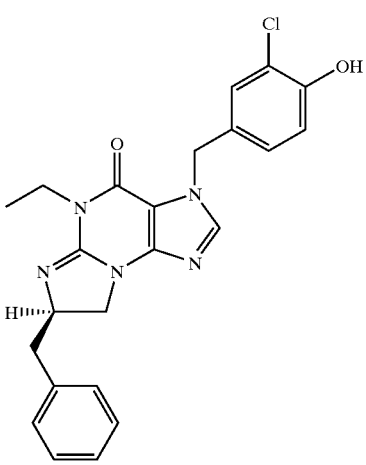

11.1.1

The product of Example 9, Step 1 (9.1.1) was demethylated using conditions of Example 4, Step 4 to yield Product 11.1.1. $^1$H NMR (300 MHz, DMSOd6) δ 8.49 (1H, s), 7.40–7.10 (7H, m), 6.90 (1H, m), 5.36 (2H, s), 4.70 (1H, m), 4.38 (1H, m), 4.17 (1H, m), 3.92 (2H, m), 3.10 (2H, m), 1.17 (3H, m).

Step 2

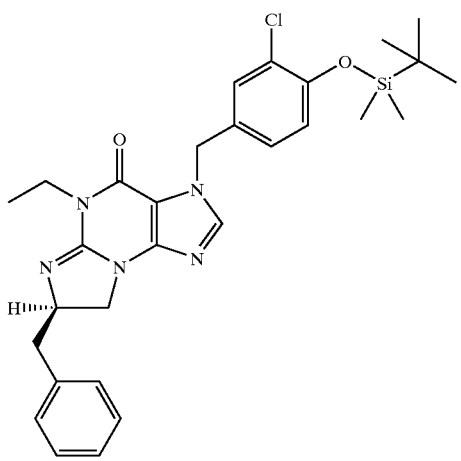
11.2.1

To a mixture of the product of Step 1 (11.1.1) (1.006 g, 2.44 mmol) and CH$_2$Cl$_2$ (15 ml) was added 2,6-lutidine (522 mg, 4.88 mmol) and tert-butyldimethylsilyl triflate (967 mg, 3.66 mmol). The mixture was stirred for 30 min, washed with sat'd NaHCO$_3$, dried (over Na$_2$SO$_4$), filtered and concentrated. The residue was subjected to flash chromatography (3:97 MeOH/CH$_2$Cl$_2$) to give the Product 11.2.1 (1.147 g, 85%). $^1$H NMR (300 MHz, CDCl$_3$) δ 7.37 (1H, s), 7.32–7.21 (6H, m), 7.12 (1H, dd, J=2.2, 8.2 Hz), 6.86 (1H, d, J=8.2 Hz), 5.32 (2H, s), 4.50 (1H, m), 4.06 (2H, m), 3.94 (1H, t, J=9.8 Hz), 3.83 (1H, m), 3.23 (1H, dd, J=4.3, 13.7 Hz), 2.72 (1H, dd, J=9.3, 13.7 Hz), 1.31 (3H, t, J=7.1Hz), 1.02 (9H, s), 0.22 (6H, s).

Step 3

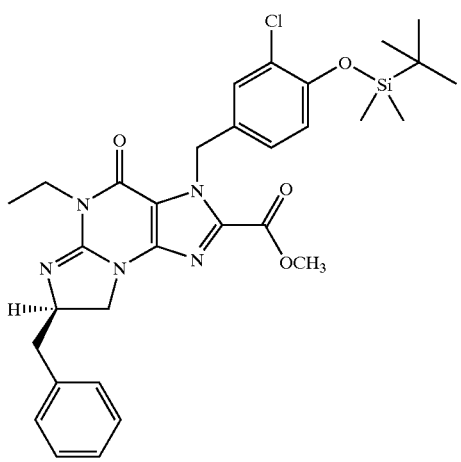
11.3.1

The product of Step 2 (11.2.1) was lithiated and reacted with methyl chloroformate according to the procedure of Example 9, Step 2 to yield Product 11.3.1. $^1$H NMR (300 MHz, CDCl$_3$) δ 7.36–7.17 (7H, m), 6.80 (1H, d, J=8.8 Hz), 5.94 (2H, s), 4.51 (1H, m), 4.08 (2H, m), 3.97 (3H, s), 3.99–3.92 (1H, m), 3.86 (1H, m), 3.23 (1H, dd, J=4.9, 13.7 Hz), 2.70 (1H, dd, J=9.3, 13.7 Hz), 1.32 (3H, t, J=7.2 Hz), 1.01 (9H, s), 0.20 (6H, s), Step 4

To a mixture of the product of Step 3 (11.3.1) (81 mg, 0.133 mmol) and THF (2.0 ml) was added 1 M TBAF in THF (0.26 ml). The mixture was stirred for 30 min prior to the addition of sat'd NaHCO$_3$ and extraction with CH$_2$Cl$_2$.

The organic phase was dried (over Na$_2$SO$_4$), filtered, concentrated and subjected to PTLC (5:95 MeOH/CH$_2$Cl$_2$) to yield the Product 11 (7.0 mg, 11%). $^1$H NMR (300 MHz, CDCl$_3$) δ 7.39 (1H, d, J=2.1 Hz), 7.38–7.17 (6H, m), 6.94 (1H, d, J=8.7 Hz), 5.93 (2H, s), 4.51 (1H, m), 4.08 (2H, m), 3.98 (3H, s), 3.96 (1H, m), 3.86 (1H, dd, J=6.5, 9.8 Hz), 3.23 (1H, dd, J=4.5, 13.2 Hz), 2.70 (1H, dd, J=9.4, 13.2 Hz), 1.32 (3H, t, J=6.9 Hz). MS (ES) m/e 494 (M+H)+.

Based on the previous examples and using techniques known to those skilled in the art, the following compounds were prepared:

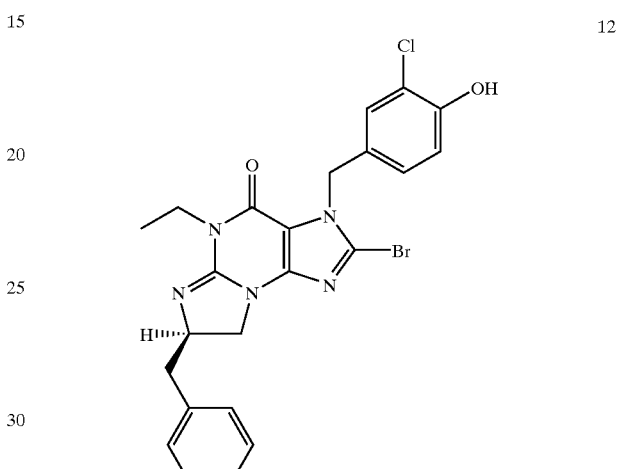
12

$^1$H NMR (300 MHz, CDCl$_3$) δ 7.43–7.16 (7H, m), 7.00–6.93 (1H, m), 5.28 (2H, s), 4.57–4.42 (1H, m), 4.17–3.76 (4H, m), 3.27–3.17 (2H, m), 2.78–2.65 (1H, m), 1.37–1.22 (3H, m). MS (ES) m/e 516 (M+H)$^+$.

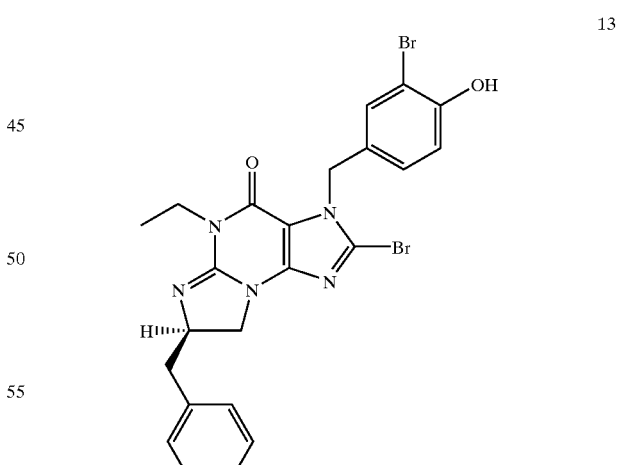
13

$^1$H NMR (300 MHz, CDCl$_3$) δ 7.53 (1H, d, J=2.2 Hz), 7.32–7.18 (6H, m.), 6.96 (1H, d, J=8.7 Hz), 5.38 (2H, s), 4.49 (1H, m), 4.04 (2H, m), 3.92 (1H, t, J=9.8 Hz), 3.81 (1H, dd, J=9.8, 7.2 Hz), 3.21 (1H, dd, J=13.5, 4.4 Hz), 2.71 (1H, dd, J=13.5, 9.3 Hz), 1.3 (3H, t, J=7.2 Hz). MS (ES) m/e 558 (M+H)$^+$.

14
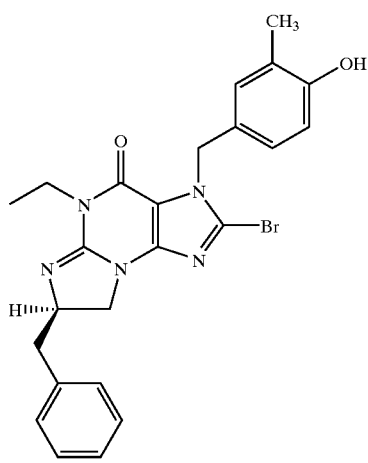
¹H NMR (CDCl₃) δ 7.35–7.15 (5H, m), 6.70 (1H, m), 5.38 (2H, s), 4.48 (1H, m), 4.15–3.78 (4H, m), 3.21 (1H, m), 2.70 (1H, m), 2.20 (3H, s), 1.31 (3H, m). MS (ES) m/e 495 (M+H)⁺.
15
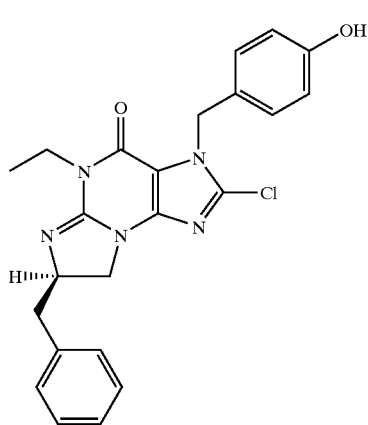
¹H NMR (300 MHz, CDCl₃) δ 7.17–7.29 (7H, m), 7.78 (2H, d), 5.38 (2H, s), 4.50 (1H, m), 3.8–4.05 (4H, m), 3.20 (1H, dd), 2.71 (1H, dd), 1.28 (3H, t). MS (ES, m/e) (M+H)⁺.
16
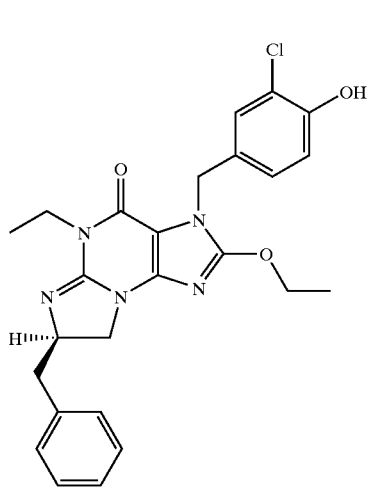
1H NMR (300 MHz, CDCl₃) δ 7.42–7.14 (7H, m), 6.93–6.86 (1H, m), 5.10 (2H, s), 4.55–4.41 (3H, m), 4.13–3.94 (2H, m), 3.93–3.82 (1H, m), 3.79–3.68 (1H, m), 3.31–3.17 (1H, m), 2.76–2.61 (1H, m), 1.48–1.36 (3H, m), 1.26 (3H, m). MS (ES) m/e 481 (M+H)⁺.
17
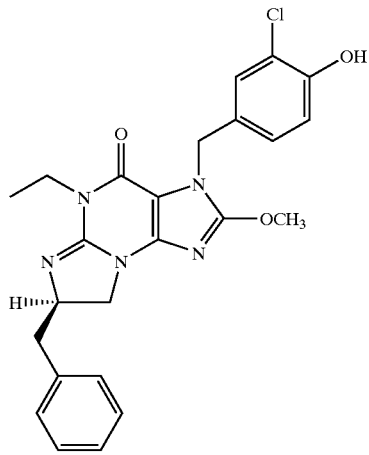
¹H NMR (300 MHz, CDCl₃) δ 7.34 (1H, s), 7.28–7.13 (6H, m), 6.81 (1H, d, J=8.0 Hz), 5.06 (2H, s), 4.41 (1H, m), 4.04 (3H, s), 4.02–3.92 (2H, m), 3.86–3.81 (2H, m), 3.81 (3H, s), 3.68 (1H, dd, J=6.5, 10.2 Hz), 3.18 (dH, dd, J=4.4, 13.2 Hz), 2.63 (1H, dd, J=9.5, 13.2 Hz), 1.25 (3H, t, J=6.6 Hz). MS (ES) m/e 466 (M+H)⁺.
18
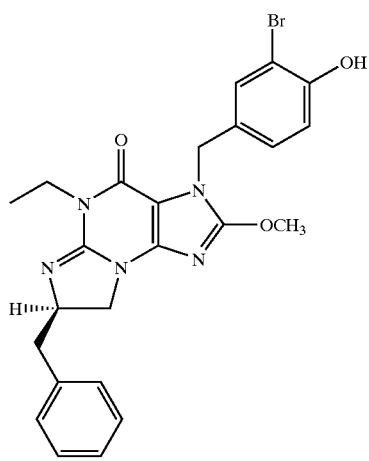
¹H NMR (300 MHz, CDCl₃) δ 7.50 (1H, d, J=1.7 Hz), 7.31–7.19 (6H, m), 6.90 (1H, d, J=8.2 Hz), 5.09 (2H, s), 4.48 (1H, m), 4.08 (3H, s), 4.01 (2H, m), 3.89 (1H, t, J=9.9 Hz), 3.74 (1H, dd, J=6.5, 9.9 Hz), 3.24 (1H, dd, J=4.3, 13.7 Hz), 2.67 (1H, dd, J=9.8, 13.7 Hz), 1.28 (3H, t, J=7.1 Hz). MS (ES) m/e 510 (M+H)⁺.

19
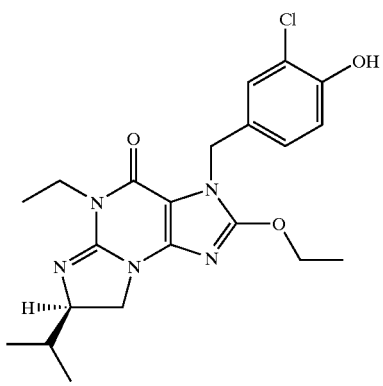
¹H NMR (CDCl₃) δ 7.36 (1H, dd), 7.19 (1H, dd), 6.88 (1H, d), 5.19 (2H, s), 4.51 (2H, q), 4.03 (4H, m), 3.77 (1H, m), 1.94 (1H, m), 1.47 (3H, t), 1.24 (3H, t), 0.94 (3H, d), 0.85 (3H, d). MS (ES) m/e 432 (M+H)⁺.
20
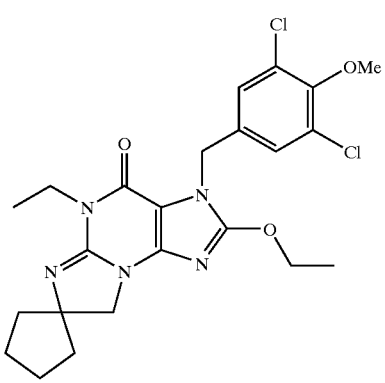
¹H NMR (300 MHz, CDCl₃) δ 7.32 (2H, s), 5.12 (2H, s), 4.50 (2H, m), 4.00 (2H, m), 3.86 (3H, s), 3.79 (2H, s), 1.8–2.0 (4H, m), 1.6–1.75 (4H, m), 1.43 (3H, t), 1.25 (3H, t). MS (ES) m/e 492 (M+H)⁺.
21
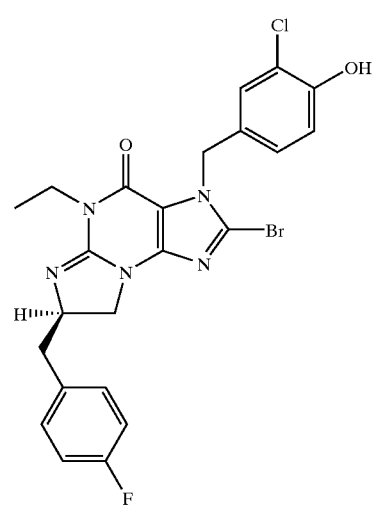
¹H NMR (CDCl₃) δ 7.38 (1H, d), 7.23–7.12 (3H, m), 7.00–6.91 (3H, m), 5.37 (2H, s), 4.45 (1H, m), 4.13–3.87 (3H, m), 3.79 (1H, m), 3.13 (1H, m), 2.72 (1H, m), 1.28 (3H, t). MS (ES) m/e 533 (M+H)⁺.
22
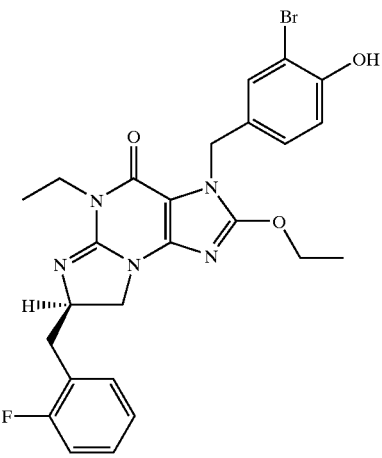
MS (ES) m/e 543 (M + H)⁺.
23
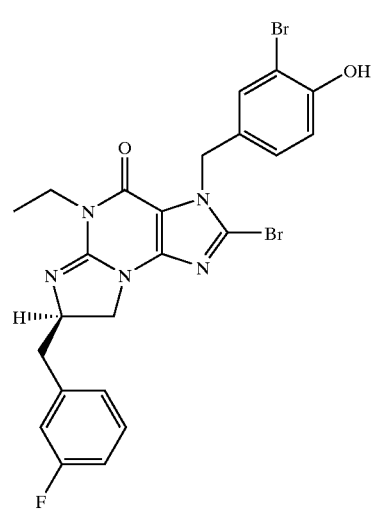
MS (ES) m/e 578 (M + H)⁺.
24
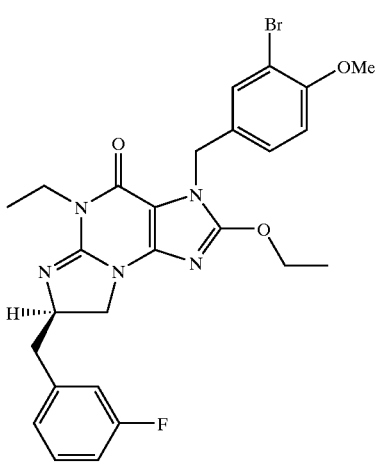
MS (ES) m/e 557 (M + H)⁺.

EXAMPLE 25

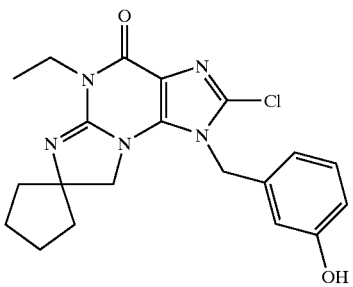

Step 1

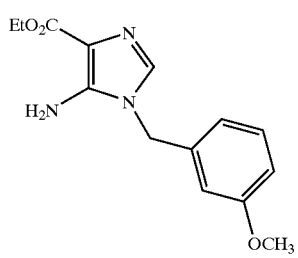

25.1.1

A mixture of ethyl aminocyanoacetate (10 g, 78 mmol) and triethyl orthoformate (11.5 g, 78 mmol) was refluxed in acetonitrile (150 ml) for 1 h. The reaction mixture was allowed to cool to RT and 3-methoxybenzylamine (10 g, 73 mmol) was added, followed by diisopropylethylamine (10 ml). The reaction mixture was refluxed for 2 h, allowed to cool, and concentrated. The residue was dissolved in 1 N HCl (200 ml) and washed with $CH_2Cl_2$ (2×100 ml). To the aqueous layer was added $NaHCO_3$ until the pH was 8. The aqueous layer was extracted with ethyl acetate and the organic extract was dried ($Na_2SO_4$), filtered and evaporated. Recrystallization of the residue (ethyl acetate) gave the Product 25.1.1 (8.5 g, 47%). $^1$H NMR (300 MHz, $CDCl_3$) δ 7.30 (1H, m), 7.14 (1H, s), 6.89 (1H, m), 6.73 (1H, m), 6.67 (1H, s), 4.96 (2H, s), 4.70 (2H, s), 3.34 (2H, m), 3.78 (3H, s), 1.39 (3H, m).

Step 2

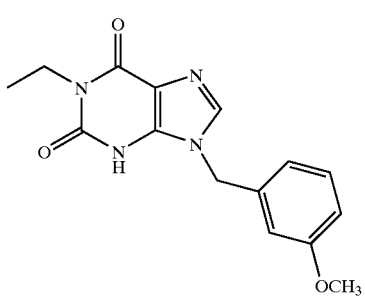

25.2.1

A mixture of 25.1.1 (8.0 g, 31 mmol), ethyl isocyanate (8.7 g, 122 mmol), triethylamine (12.3 g, 122 mmol) and toluene (80 ml) was heated at 100° C. in a sealed tube overnight. The solvent was concentrated to about 40 ml and the residue was cooled in ice. The precipitate was collected, washed with ether and dried. The precipitate was dissolved in methanol (120 ml) and sodium methoxide (6.5 g, 122 mmol) was added. The reaction mixture was refluxed for 3 h. Methanol was removed and the residue was dissolved in water (100 ml). The solution was acidified to pH 5 and the resultant white precipitate was collected, washed with water and dried under vacuum to give the Product 25.2.1 (8.7 g, 94%). $^1$H NMR (300 MHz, $CD_3OD$) δ 8.03 (1H, s), 7.16 (1H, m), 6.80–6.67 (3H, m), 5.14 (2H, s), 3.88 (2H, m), 3.65 (3H, s), 1.08 (3H, m).

Step 3

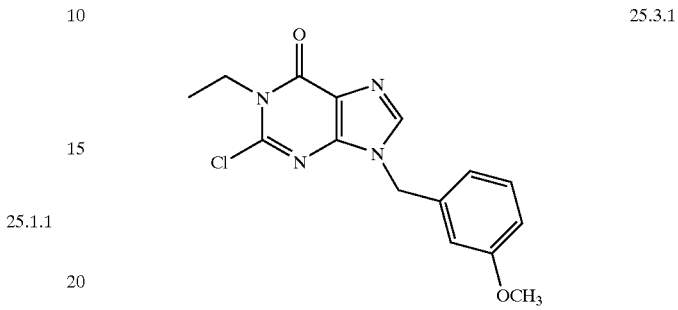

25.3.1

25.2.1 (7.7g, 27 mmole) in phosphorus oxychloride (100 ml) was refluxed for 5 h. Phosphorus oxychloride was removed via vacuum and the residue was dissolved in ethyl acetate (200 ml). The solution was washed with saturated $NaHCO_3$ and dried over $Na_2SO_4$. The product was subjected to flash chromatography (1:5 ethyl acetate/hexane) to give the Product 25.3.1 (4.3 g, 53%). $^1$H NMR (300 MHz, $CDCl_3$) δ 7.71 (1H, s), 7.29 (1H, m), 6.9–6.8 (3H, m), 5.24 (2H, s), 4.21 (2H, m), 3.80 (3H, s), 1.40 (3H, m).

Step 4

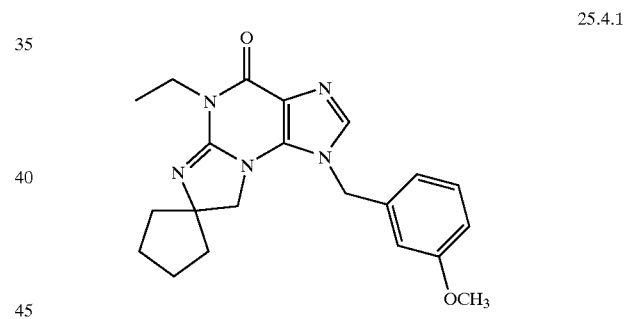

25.4.1

A mixture of Product 25.3.1 (100 mg, 0.31 mmol), 1-amino-1-cyclopentanemethanol (109 mg, 0.94 mmol) and diisopropylethylamine (160 mg, 12.4 mmol) in 1 ml NMP (1 ml) was heated at 110° C. overnight. Water (5 ml) was added and the reaction was cooled in ice. The resultant white precipitate was collected by filtration, washed with water and dried under vacuum. To the precipitate in $CH_2Cl_2$ (15 ml) was added methanesulfonyl chloride (102 mg, 0.94 mmol) and triethylamine (156 mg, 1.55 mmol). The mixture was stirred at RT overnight. $CH_2Cl_2$ (40 ml) was added and the whole was washed with water, dried ($Na_2SO_4$), filtered and evaporated. The residue was subjected to PTLC (90:10 $CH_2Cl_2$/MeOH) to give the Product 25.4.1. $^1$H NMR (300 MHz, $CDCl_3$) δ 7.38–7.24 (2H, m), 6.90 (1H, m), 6.60 (2H, m), 5.22 (2H, s), 4.04 (2H, m), 3.78 (3H, s), 3.67 (2H, s), 1.9–1.7 (4H, m), 1.6–1.4 (4H, m), 1.24 (3H, m). MS (ES, m/e) 380 (M+1).

Step 5

The product of Step 4 (25.4.1) (25 mg, 0.07 mmol) was dissolved in $CH_2Cl_2$ (5 ml) and N-chlorosuccinimide (13 mg, 0.10 mmol) was added. The reaction mixture was heated at 65° C. for 16 h. The solvent was removed and the residue was subjected to PTLC (95:5 CH$_2$Cl$_2$/MeOH) to give the product. To this product in CH$_2$Cl$_2$ (5 ml) was added boron tribromide (0.05 ml). The white cloudy suspension was stirred at RT for 2.5 h. Saturated NaHCO$_3$ solution (10 ml) was added and the whole was extracted with CH$_2$Cl$_2$ (25 ml), dried (Na$_2$SO$_4$), filtered and evaporated. The Product 25 was obtained after PTLC (90:10 CH$_2$Cl$_2$/MeOH). $^1$H NMR (300 MHz, CDCl$_3$) δ 7.27 (1H, m), 6.87 (1H, m), 6.71 (1H, m), 6.51 (1H, s), 5.28 (2H, s), 3.91 (2H, m), 3.70 (2H, s), 1.7–1.9 (4H, m), 1.4–1.6 (4H, m), 1.14 (3H, m). MS (ES) m/e 400 (M+H)$^+$.

EXAMPLE 26

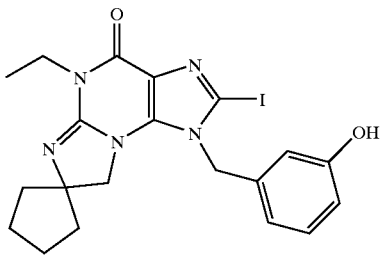

26

The Product 26 was prepared by reaction of Product 25.4.1 with N-iodosuccinimide followed by demethylation of the product with boron tribromide. $^1$H NMR (300 MHz, CDCl$_3$) δ 6.98 (1H, m), 6.56 (1H, m), 6.27 (1H, m), 6.20 (1H, s), 5.03 (2H, s), 3.72 (2H, m), 3.50 (2H, s), 1.45–1.6 (4H, m), 1.20–1.35 (4H, m), 0.99 (3H, m). MS (ES) m/e 492 (M+H)$^+$.

EXAMPLE 27

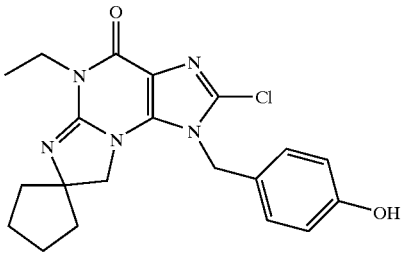

27

Step 1

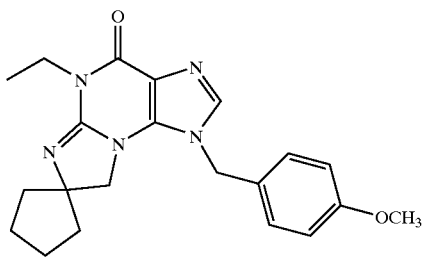

27.1.1

The Product 27.1.1 was prepared using the same sequence of reactions as described for 25.4.1, except that 4-methoxybenzylamine was used in place of 3-methoxybenzylamine in the first step.

Step 2

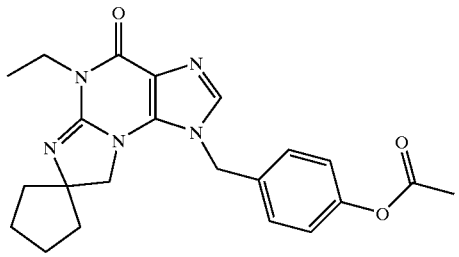

27.2.1

To a stirred, ice-cold mixture of 27.1.1 (409 mg, 1.1 mmol) in CH$_2$Cl$_2$ (40 ml) was added boron tribromide (0.26 ml, 2.7 mmol). After 2 h, the reaction mixture was poured into sat'd NaHCO$_3$. The solid was collected and the filtrate was extracted three times with CH$_2$Cl$_2$. The combined organic layers were dried over Na$_2$SO$_4$, filtered and evaporated. PTLC (93:7 CH$_2$Cl$_2$/MeOH) of the residue gave the product. To the product was added CH$_2$Cl$_2$ (5 ml), Et$_3$N (0.3 ml, 2 mmol), acetic anhydride (0.2 ml, 2 mmol) and (4-dimethylamino)pyridine (2 mg), and the reaction mixture was stirred for 4 h. Sat'd NaHCO$_3$ was added and the whole was extracted three times with CH$_2$Cl$_2$. The combined organic layers were dried over Na$_2$SO$_4$, filtered and evaporated to give the Product 27.2.1.

Step 3

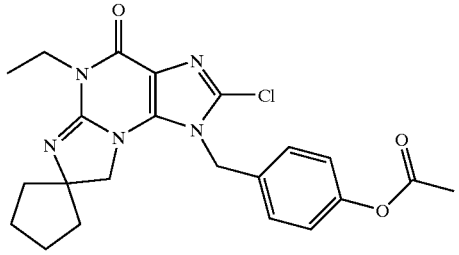

27.3.1

A mixture of 27.2.1 (42 mg, 0.10 mmol) and N-chlorosuccinimide (28 mg, 0.21 mmol) in CH$_2$Cl$_2$ (5 ml) was stirred for 16 h. The reaction mixture was concentrated, then subjected to PTLC (95:5 CH$_2$Cl$_2$/MeOH) to give the Product 27.3.1 (13 mg, 29%). $^1$H NMR (300 MHz, CDCl$_3$) δ 7.15 (2H, d, J=8.5 Hz), 7.07 (2H, d, J=8.5 Hz), 5.28 (2H, s), 4.02 (2H, q, J=6.9 Hz), 3.65 (2H, s), 2.29 (3H, s), 1.82 (4H, m), 1.50 (4H, m), 1.24 (3H, t, J=6.9 Hz). MS (ES) m/e 486.1 (M+H)$^+$.

Step 4

A mixture of the Product 27.3.1 (7 mg, 0.02 mmol) and sat'd NaHCO$_3$ (0.5 ml) in MeOH (2 ml) was stirred for 2 h. Sat'd NaCl and water were added and the whole was extracted three times with CH$_2$Cl$_2$. The combined organic layers were dried over Na$_2$SO$_4$, filtered and evaporated. The product 27 (2 mg, 20%) was obtained after PTLC (93:7 CH$_2$Cl$_2$/MeOH). $^1$H NMR (300 MHz, CDCl$_3$) δ 6.90 (4H, m). 5.22 (2H, s), 4.02 (2H, q, J=6.9 Hz), 3.67 (2H, s), 1.82 (4H, m), 1.50 (4H, m), 1.24 (3H, t, J=6.9 Hz). MS (ES) m/e 400.1 (M+H)$^+$.

The above description is not intended to detail all modifications and variations of the invention. It will be appreciated by those skilled in the art that changes can be made to the embodiments described above without departing from the inventive concept. It is understood, therefore, that the invention is not limited to the particular embodiments

What is claimed is:
1. A compound selected from the group consisting of:
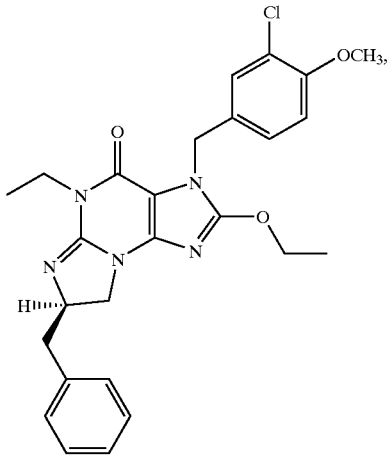
1
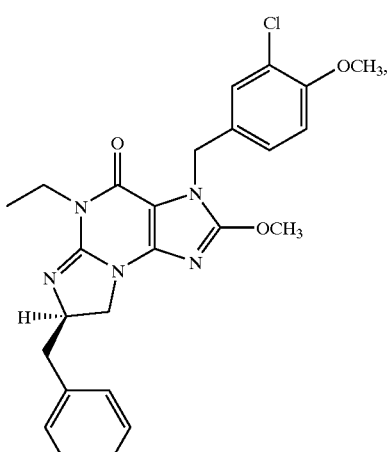
2
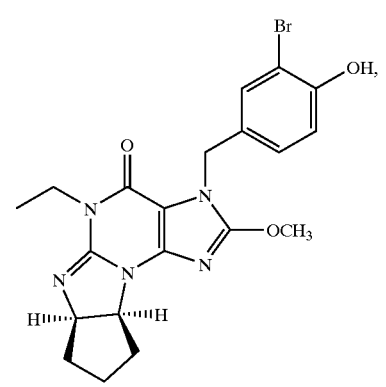
5
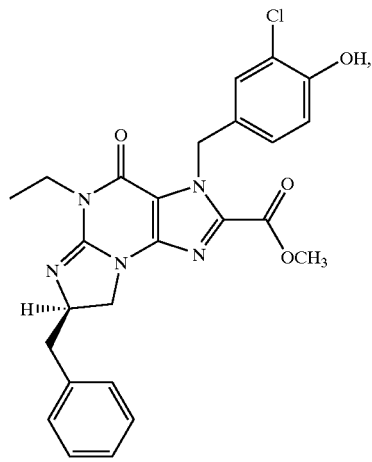
11
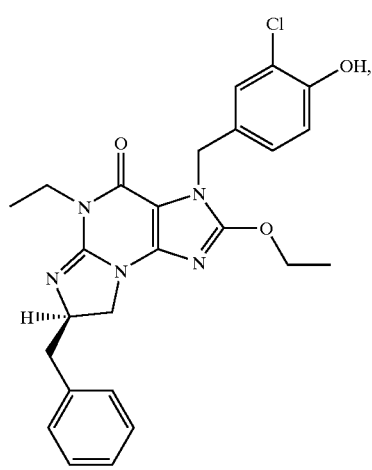
16
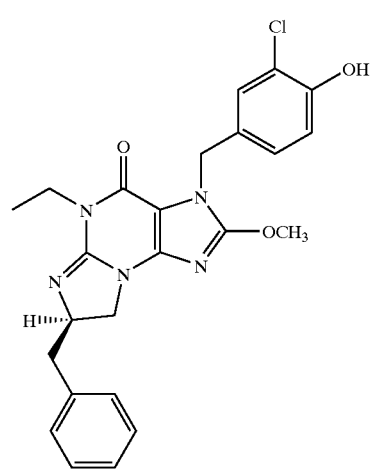
17

-continued
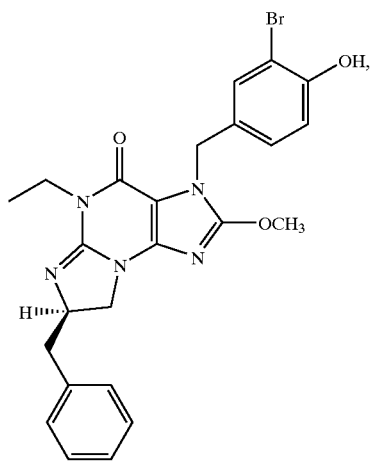
18
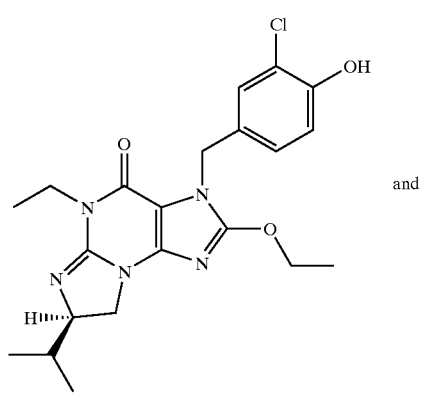
and
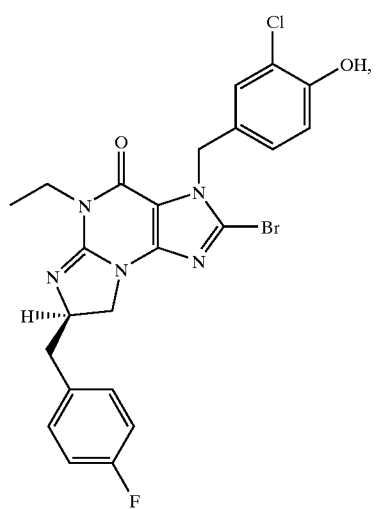
or a pharmaceutically acceptable salt or solvate thereof.
2. The compound according to claim 1 which is:
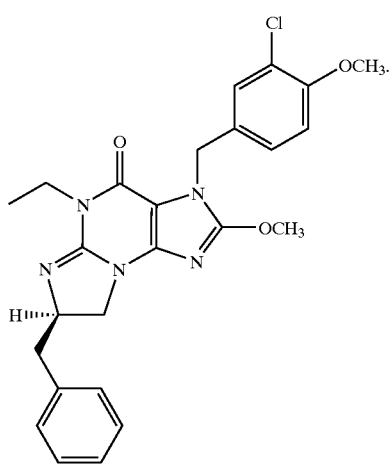
2
3. The compound according to claim 1 which is:
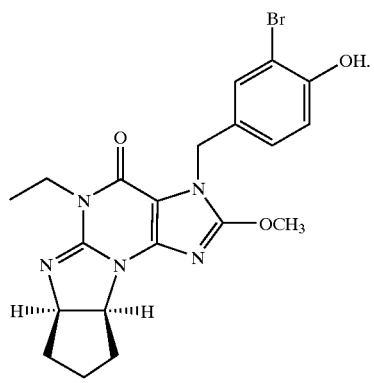
5
4. The compound according to claim 1 which is:
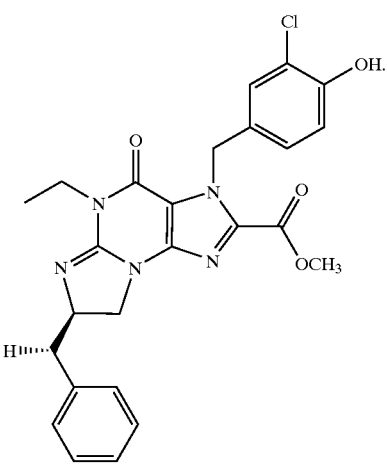
11

5. The compound according to claim 1 which is:

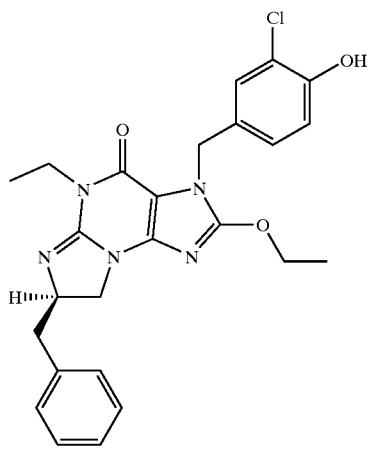

16

6. The compound according to claim 1 which is:

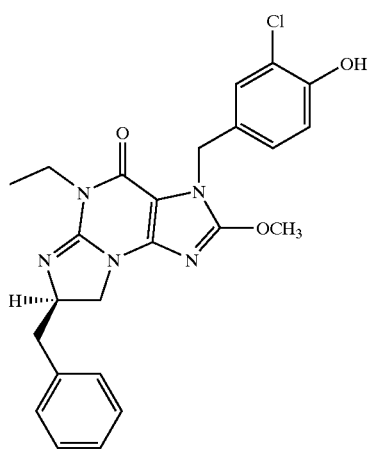

17

7. The compound according to claim 1 which is:

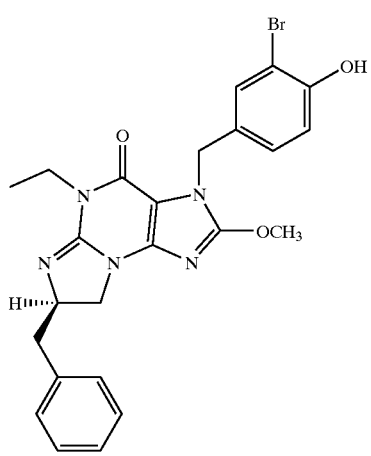

18

8. A pharmaceutical composition comprising the compound of claim 1 or a salt or solvate thereof and a pharmaceutically acceptable carrier.

9. The composition according to claim 8, wherein the compound of claim 1, salt or solvate thereof is administered to a patient in an amount ranging from about 1 to about 1000 milligrams per day.

10. The compound according to claim 1 which is:

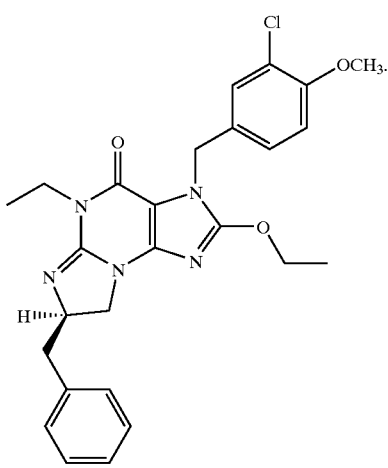

1

11. The compound according to claim 1 which is:

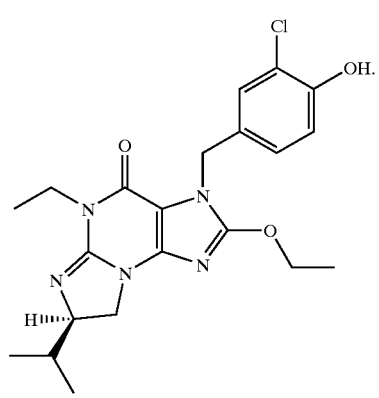

19

12. The compound according to claim 1 which is:

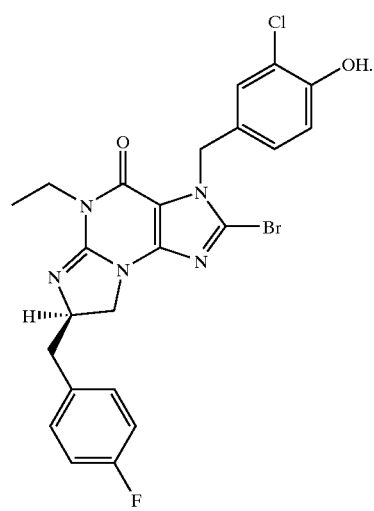

21

13. A compound selected from the group consisting of:
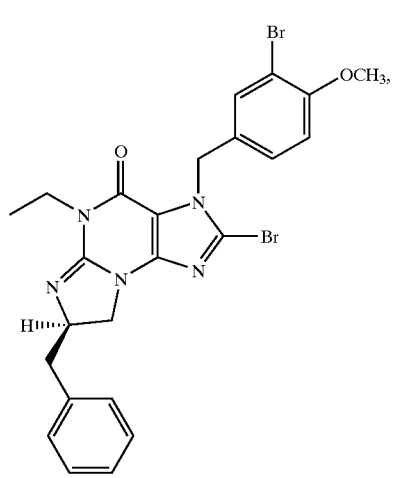
1.3.2
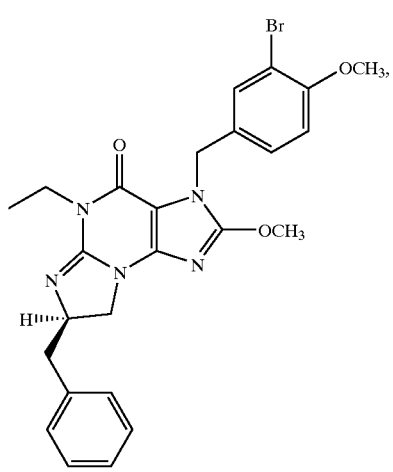
3
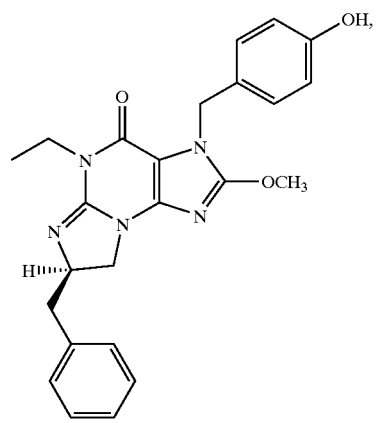
8
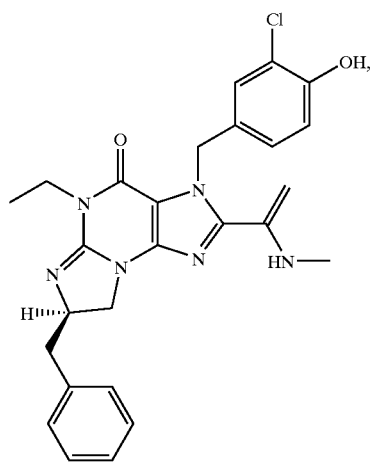
9
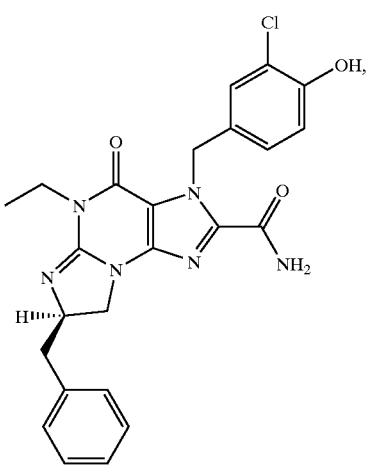
10
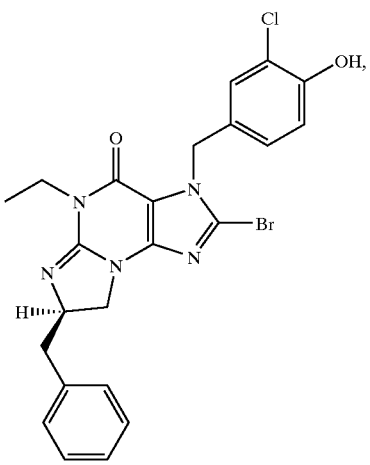
12

-continued
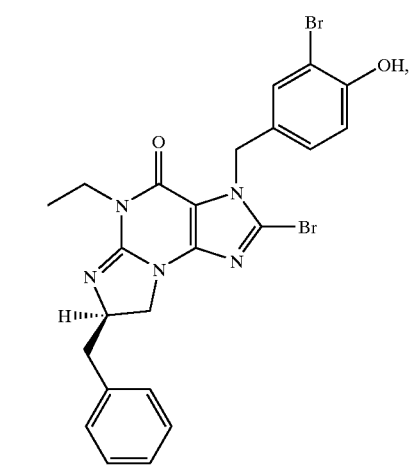
13
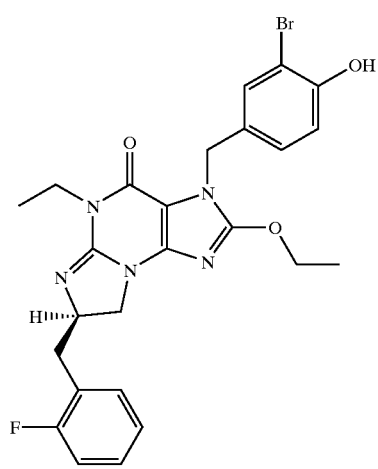
22
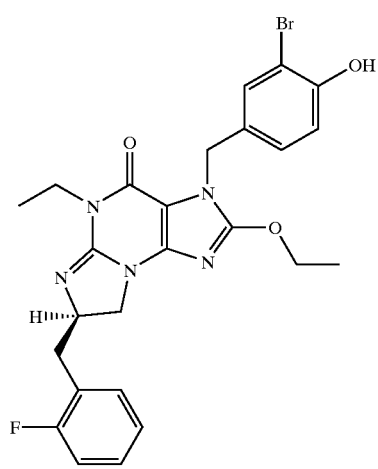
and
23
14. A compound selected from the group consisting of:
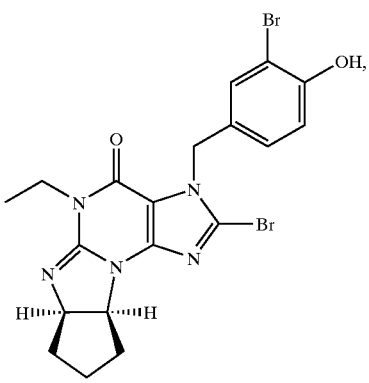
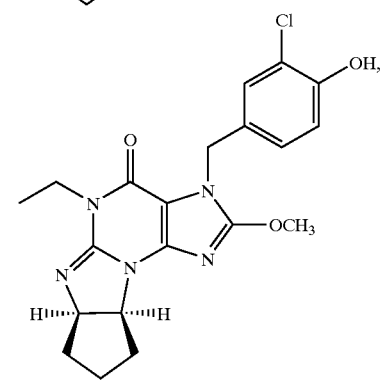
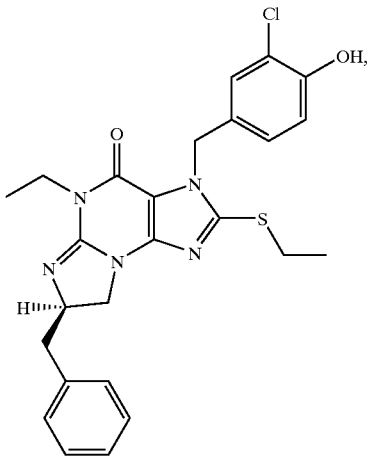
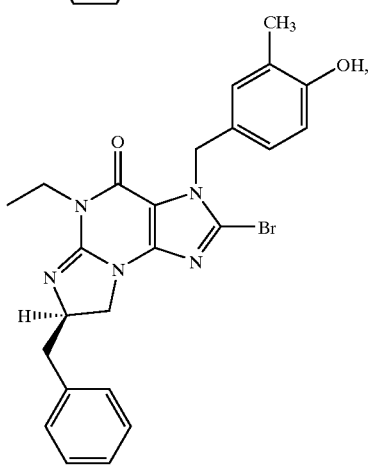
or a pharmaceutically acceptable salt or solvate thereof.

-continued
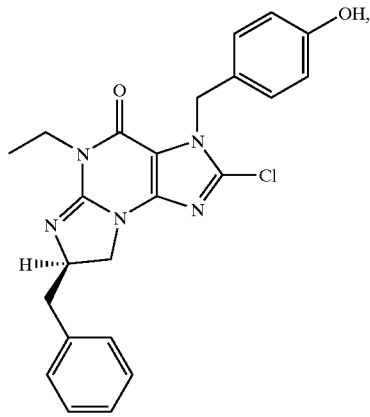
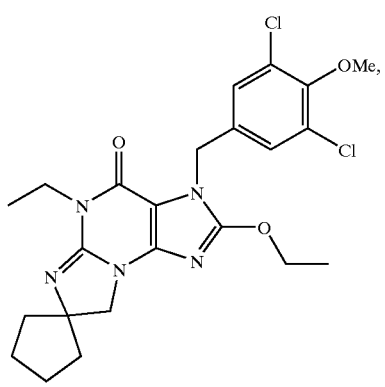
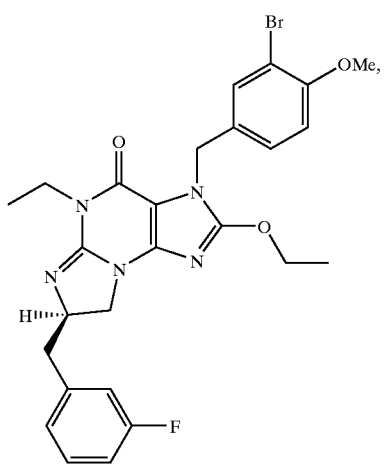
-continued
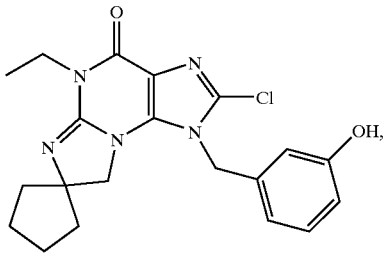
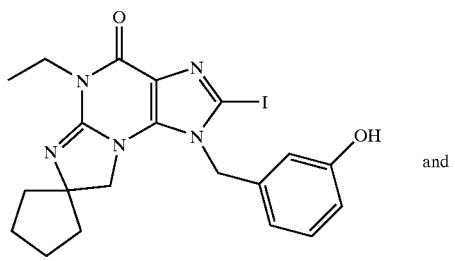
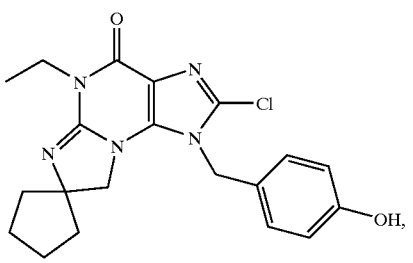
or a pharmaceutically acceptable salt or solvate thereof.
* * * * *